US009169510B2

(12) United States Patent  
Ju et al.

(10) Patent No.: US 9,169,510 B2
(45) Date of Patent: Oct. 27, 2015

(54) PYROSEQUENCING METHODS AND RELATED COMPOSITIONS

(75) Inventors: Jingyue Ju, Englewood Cliffs, NJ (US); Jian Wu, New York, NY (US); Dae H. Kim, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 945 days.

(21) Appl. No.: 11/922,385

(22) PCT Filed: Jun. 20, 2006

(86) PCT No.: PCT/US2006/024157
§ 371 (c)(1),
(2), (4) Date: Jul. 29, 2009

(87) PCT Pub. No.: WO2007/002204
PCT Pub. Date: Jan. 4, 2007

(65) Prior Publication Data
US 2009/0325154 A1    Dec. 31, 2009

Related U.S. Application Data

(60) Provisional application No. 60/692,816, filed on Jun. 21, 2005.

(51) Int. Cl.
*C12Q 1/68* (2006.01)
*C07H 21/02* (2006.01)
*G01N 31/22* (2006.01)
*G01N 33/52* (2006.01)
*C12M 1/00* (2006.01)
*C12M 1/34* (2006.01)
*C12M 3/00* (2006.01)
*C12Q 1/66* (2006.01)
*G01N 33/53* (2006.01)
*G01N 33/543* (2006.01)

(52) U.S. Cl.
CPC *C12Q 1/66* (2013.01); *C12Q 1/686* (2013.01); *C12Q 1/6869* (2013.01); *G01N 33/5308* (2013.01); *G01N 33/54353* (2013.01); *C12Q 2334/20* (2013.01)

(58) Field of Classification Search
USPC ............... 435/6.1, 283.1, 287.2; 536/23.1; 422/430
See application file for complete search history.

(56) References Cited

U.S. PATENT DOCUMENTS

| 4,711,955 A | 12/1987 | Ward et al. |
| 4,824,775 A | 4/1989 | Dattagupta |
| 5,118,605 A | 6/1992 | Urdea |
| 5,174,962 A | 12/1992 | Brennan |
| 5,302,509 A | 4/1994 | Cheeseman |
| 5,599,675 A | 2/1997 | Brenner |
| 5,654,419 A | 8/1997 | Mathies |
| 5,728,528 A | 3/1998 | Mathies |
| 5,763,594 A | 6/1998 | Hiatt |
| 5,770,367 A | 6/1998 | Southern |
| 5,789,167 A | 8/1998 | Konrad |
| 5,804,386 A | 9/1998 | Ju |
| 5,808,045 A | 9/1998 | Hiatt |
| 5,814,454 A | 9/1998 | Ju |
| 5,834,203 A | 11/1998 | Katzir |
| 5,849,542 A | 12/1998 | Reeve et al. |
| 5,853,992 A | 12/1998 | Glazer |
| 5,869,255 A | 2/1999 | Mathies |
| 5,872,244 A | 2/1999 | Hiatt |
| 5,876,936 A | 3/1999 | Ju |
| 5,885,775 A | 3/1999 | Haff et al. |
| 5,945,283 A | 8/1999 | Kwok |
| 5,952,180 A | 9/1999 | Ju |
| 6,028,190 A | 2/2000 | Mathies |
| 6,046,005 A | 4/2000 | Ju |
| 6,074,823 A | 6/2000 | Koster |
| 6,087,095 A | 7/2000 | Rosenthal et al. |
| 6,136,543 A | 10/2000 | Anazawa et al. |
| 6,197,557 B1 | 3/2001 | Markarov et al. |
| 6,210,891 B1 * | 4/2001 | Nyren et al. ............... 435/6 |
| 6,214,987 B1 | 4/2001 | Hiatt |
| 6,218,118 B1 | 4/2001 | Sampson |
| 6,218,530 B1 | 4/2001 | Rothschild et al. |
| 6,232,465 B1 | 5/2001 | Hiatt |
| 6,312,893 B1 | 11/2001 | Van Ness et al. |
| 6,316,230 B1 | 11/2001 | Egholm et al. |
| 6,361,940 B1 | 3/2002 | Van Ness et al. |
| 6,613,508 B1 | 9/2003 | Ness et al. |
| 6,627,748 B1 | 9/2003 | Ju et al. |
| 6,664,079 B2 | 12/2003 | Ju et al. |

(Continued)

FOREIGN PATENT DOCUMENTS

CA      2425112      9/2011
DE      20122767 U1  8/2012

(Continued)

OTHER PUBLICATIONS

Datasheet Luciferase, Down loaded from the internet [www.sigmaaldrich.com], 2011, printed on Jul. 1, 2011, pp. 1 and 2.*
Pernodet et al, Pore size of agarose gels by atomic force microscopy, 1997, Electrophoresis, 18, 55-58.*
Ju J., et al. (2006) Four color DNA sequencing by synthesis using cleavable fluorescent nucleotide reversible terminators. Proc Natl Acad Sci USA 103: 19635 40.
Notification Concerning Transmittal of International Preliminary Report on Patentability issued Mar. 19, 2009 in connection with International Application No. PCT/US06/024157.

(Continued)

*Primary Examiner* — Narayan Bhat
(74) *Attorney, Agent, or Firm* — John P. White; Cooper & Dunham LLP

(57) ABSTRACT

This invention provides methods for pyrosequencing and compositions comprising 3'-O— modified deoxynucleoside triphosphates.

6 Claims, 19 Drawing Sheets

(56) References Cited

U.S. PATENT DOCUMENTS

| | | |
|---|---|---|
| 6,664,399 B1 | 12/2003 | Sebasan |
| 6,787,308 B2 | 9/2004 | Balasubramanian et al. |
| 6,833,246 B2 | 12/2004 | Balasubramanian et al. |
| 7,057,026 B2 | 6/2006 | Barnes et al. |
| 7,057,031 B2 | 6/2006 | Olejnik et al. |
| 7,074,597 B2 | 7/2006 | Ju |
| 7,345,159 B2 | 3/2008 | Ju |
| 7,622,279 B2 | 11/2009 | Ju |
| 7,635,578 B2 | 12/2009 | Ju et al. |
| 7,713,698 B2 | 5/2010 | Ju et al. |
| 7,790,869 B2 | 9/2010 | Ju et al. |
| 7,883,869 B2 | 2/2011 | Ju et al. |
| 7,982,029 B2 | 7/2011 | Ju et al. |
| 8,088,575 B2 | 1/2012 | Ju et al. |
| 8,298,792 B2 | 10/2012 | Ju et al. |
| 8,796,432 B2 | 8/2014 | Ju et al. |
| 8,889,348 B2 | 11/2014 | Ju |
| 2002/0012966 A1 | 1/2002 | Shi et al. |
| 2002/0102586 A1* | 8/2002 | Ju et al. ............... 435/6 |
| 2002/0168642 A1 | 11/2002 | Drukier |
| 2003/0008285 A1 | 1/2003 | Fischer |
| 2003/0022225 A1 | 1/2003 | Montforte et al. |
| 2003/0027140 A1 | 2/2003 | Ju et al. |
| 2003/0044871 A1 | 3/2003 | Cutsforth et al. |
| 2003/0054360 A1 | 3/2003 | Gold et al. |
| 2003/0099972 A1 | 5/2003 | Olejnik et al. |
| 2003/0134807 A1* | 7/2003 | Hardin et al. .......... 514/44 |
| 2003/0166282 A1 | 9/2003 | Brown et al. |
| 2003/0190680 A1 | 10/2003 | Rothschild et al. |
| 2003/0198982 A1 | 10/2003 | Seela et al. |
| 2004/0185466 A1 | 9/2004 | Ju et al. |
| 2005/0032081 A1 | 2/2005 | Ju et al. |
| 2005/0239134 A1 | 10/2005 | Gorenstein et al. |
| 2006/0003352 A1 | 1/2006 | Lipkin et al. |
| 2006/0057565 A1 | 3/2006 | Ju et al. |
| 2006/0105461 A1 | 5/2006 | Tom-Moy et al. |
| 2006/0240439 A1 | 10/2006 | Smith et al. |
| 2006/0252038 A1 | 11/2006 | Ju |
| 2006/0252938 A1 | 11/2006 | Sava et al. |
| 2007/0275387 A1 | 11/2007 | Ju et al. |
| 2008/0131895 A1 | 6/2008 | Ju et al. |
| 2008/0199868 A1 | 8/2008 | Ju et al. |
| 2008/0319179 A1 | 12/2008 | Ju et al. |
| 2009/0088332 A1 | 4/2009 | Ju et al. |
| 2009/0240030 A1 | 9/2009 | Ju et al. |
| 2009/0263791 A1 | 10/2009 | Ju et al. |
| 2009/0298072 A1 | 12/2009 | Ju et al. |
| 2011/0014611 A1 | 1/2011 | Ju et al. |
| 2011/0039259 A1 | 2/2011 | Ju et al. |
| 2012/0142006 A1 | 6/2012 | Ju et al. |
| 2012/0156680 A1 | 6/2012 | Ju et al. |
| 2013/0264207 A1 | 10/2013 | Ju et al. |
| 2013/0280700 A1 | 10/2013 | Ju et al. |
| 2014/0093869 A1 | 4/2014 | Ju et al. |
| 2014/0206553 A1 | 7/2014 | Ju et al. |
| 2014/0315191 A1 | 10/2014 | Ju et al. |

FOREIGN PATENT DOCUMENTS

| | | |
|---|---|---|
| EP | 0992511 | 4/2000 |
| EP | 1337541 B1 | 3/2007 |
| EP | 1790736 A2 | 5/2007 |
| EP | 2209911 B1 | 10/2013 |
| GB | WO2004/018497 A2 * | 3/2004 |
| GB | 2446083 | 3/2011 |
| GB | 2446084 | 3/2011 |
| GB | 2457402 | 9/2011 |
| WO | WO 91/06678 | 5/1991 |
| WO | WO 92/10587 | 6/1992 |
| WO | WO 00/53805 | 9/2000 |
| WO | WO 01/27625 | 4/2001 |
| WO | WO 01/92284 | 12/2001 |
| WO | WO 02/22883 | 3/2002 |
| WO | WO 02/22883 A1 | 3/2002 |
| WO | WO 02/29003 | 4/2002 |
| WO | WO 02/079519 | 10/2002 |
| WO | WO 02/079519 A1 | 10/2002 |
| WO | WO 2004/007773 | 1/2004 |
| WO | WO 2004/055160 | 1/2004 |
| WO | WO/2004/018493 | 3/2004 |
| WO | WO/2004/018497 | 3/2004 |
| WO | WO 2005/084367 | 9/2005 |
| WO | WO 2006/073436 | 7/2006 |
| WO | WO 2007/002204 | 1/2007 |
| WO | WO/2007/053702 | 5/2007 |
| WO | WO/2007/053719 | 5/2007 |
| WO | WO/2007/062105 | 5/2007 |
| WO | WO 2009/051807 A1 | 4/2009 |
| WO | WO 2012/162429 | 11/2012 |
| WO | WO 2013/154999 | 10/2013 |
| WO | WO 2013/191793 | 12/2013 |
| WO | WO 2014/144883 | 11/2014 |
| WO | WO 2014/144898 | 11/2014 |

OTHER PUBLICATIONS

Notice of Allowance issued Feb. 24, 2009 in connection with U.S. Appl. No. 11/894,690.

Notice of Allowance issued Mar. 23, 2009 in connection with U.S. Appl. No. 11/894,808.

Ronaghi, M., et al. Real-time DNA sequencing using detection of pyrophosphate release. Anal Biochem. Nov. 1, 1996;242(1):84-9.

Kim, S., et al. Solid phase capturable dideoxynucleotides for multiplex genotyping using mass spectrometry. Nucleic Acids Res. Aug. 15, 2002;30(16):e85.

Hanshaw, R.G., et al. An indicator displacement system for fluorescent detection of phosphate oxyanions under physiological conditions. Tetrahedron Letters. Nov. 15, 2004:45(1):8721-8724.

Sep. 16, 2012 Petition for Inter Partes Review of U.S. Pat. No. 7,790,869.

Sep. 17, 2012 Motion to Waive Page Limit and Proposed Petition in connection with Petition for Inter Partes Review of U.S. Pat. No. 7,790,869.

Dec. 21, 2012 Preliminary Response under 37 C.F.R. 42.107 in connection with IPR2012-00007.

Mar. 12, 2013 Decision on Petition for Inter Partes Review in connection with IPR2012-00007.

Mar. 26, 2013 Request for Reconsideration in connection with IPR2012-00007.

Mar. 26, 2013 Request for Rehearing under 37 C.F.R. 42.71 of Decision to Institute Inter Partes Review in connection with IPR2012-00007.

Apr. 26, 2013 Opposition to Request for Reconsideration (Rehearing) Under 37 C.F.R. 42.71.(C) in connection with IPR2012-00007.

May 10, 2013 Decision on Request for Rehearing in connection with IPR2012-00007.

Aug. 30, 2013 Substitute Patent Owner Response Under 37 C.F.R. 42.120 in connection with IPR2012-00007.

Aug. 30, 2013 Substitute Patent Owner Motion to Amend Under 37 C.F.R. 42.121 in connection with IPR2012-00007.

Sep. 27, 2013 Petitioner Opposition to Motion to Amend in connection with IPR2012-00007.

Sep. 27, 2013 Petitioner Reply to Response to Petition in connection with IPR2012-00007.

Oct. 28, 2013 Patentee Reply on Motion to Amend in connection with IPR2012-00007.

Exhibit 1001, filed Sep. 16, 2012 in connection with IPR2012-00007: U.S. Pat. No. 7,790,869 issued Sep. 7, 2010 to Ju et al.

Exhibit 1002, filed Sep. 16, 2012 in connection with IPR2012-00007: PCT International Application No. PCT/US90/06678 filed Oct. 26, 1990, published on May 16, 1991 as Publication No. WO 91/06678 to SRI International.

Exhibit 1003, filed Sep. 16, 2012 in connection with IPR2012-00007: Prober et al. (1987), "A System for Rapid DNA Sequencing with Fluorescent Chain-Terminating Dideoxynucleotides", *Science* vol. 238, Oct. 16, 1987, pp. 336-341.

Exhibit 1004, filed Sep. 16, 2012 in connection with IPR2012-00007: U.S. Pat. No. 5,242,796 issued Sep. 7, 1993 to Prober et al.

(56) References Cited

OTHER PUBLICATIONS

Exhibit 1005, filed Sep. 16, 2012 in connection with IPR2012-00007: U.S. Pat. No. 5,547,839 issued Aug. 20, 1996 to Dower et al.
Exhibit 1006, filed Sep. 16, 2012 in connection with IPR2012-00007: PCT International Application No. PCT/US96/02342 filed Feb. 21, 1996, published on Sep. 6, 1996 as Publication No. WO 96/27025 to Ely Rabani.
Exhibit 1007, filed Sep. 16, 2012 in connection with IPR2012-00007: PCT International Application No. PCT/GB00/00873 filed Mar. 10, 2000, published on Sep. 14, 2000 as Publication No. WO 00/53805 to ASM Scientific, Inc.
Exhibit 1008, filed Sep. 16, 2012 in connection with IPR2012-00007: U.S. Pat. No. 7,270,951 issued Sep. 18, 2007 to Stemple et al.
Exhibit 1009, filed Sep. 16, 2012 in connection with IPR2012-00007: U.S. Application for A Method for Direct Nucleic Acid Sequencing; U.S. Appl. No. 09/266,187, filed Mar. 10, 1999.
Exhibits 1010-1012, filed Sep. 16, 2012 in connection with IPR2012-00007: PCT International Application No. PCT/JP97/00239, filed Jan. 31, 1997, published on Aug. 6, 1998 as Publication No. WO 98/33939 to Hitachi, Ltd. with certified English translation, and Translation Affidavit.
Exhibit 1013, filed Sep. 16, 2012 in connection with IPR2012-00007: U.S. Pat. No. 5,047,519 issued Sep. 10, 1991 to Hobbs, Jr. et al.
Exhibit 1014, filed Sep. 16, 2012 in connection with IPR2012-00007: U.S. Pat. No. 4,804,748 issued Feb. 14, 1989 to Seela.
Exhibit 1015, filed Sep. 16, 2012 in connection with IPR2012-00007: U.S. Pat. No. 5,844,106 issued Dec. 1, 1998 to Seela et al.
Exhibit 1016, filed Sep. 16, 2012 in connection with IPR2012-00007: PCT International Application No. PCT/US89/02170, filed May 18, 1989, published on Nov. 30, 1989 as Publication No. WO 89/11548 to Cetus Corporation.
Exhibit 1017, filed Sep. 16, 2012 in connection with IPR2012-00007: U.S. Pat. No. 7,037,687 issued May 2, 2006 to Williams et al.
Exhibit 1018, filed Sep. 16, 2012 in connection with IPR2012-00007: U.S. Pat. No. 6,255,083 issued Jul. 3, 2001 to Williams.
Exhibit 1019, filed Sep. 16, 2012 in connection with IPR2012-00007: U.S. Pat. No. 6,001,566 issued Dec. 14, 1999 to Canard et al.
Exhibit 1020, filed Sep. 16, 2012 in connection with IPR2012-00007: PCT International Application No. PCT/GB93/00848, filed Apr. 22, 1993, published as Oct. 28, 1993 as Publication No. WO 93/21340 to Medical Research Council.
Exhibit 1021, filed Sep. 16, 2012 in connection with IPR2012-00007: Sep. 15, 2012 Declaration of George Weinstock Under Rule 37 C.F.R. §1.132.
Exhibit 1022, filed Sep. 16, 2012 in connection with IPR2012-00007: Excerpts of File History of U.S. Pat. No. 7,790,869.
Exhibit 1025, filed Apr. 30, 2013 in connection with IPR2012-00007: Columbia's Amended Complaint from The Trustees of Columbia University in the *City of New York* v. *Illumina, Inc.*, D. Del C.A. No. 12-376 (GMS), filed Apr. 11, 2012.
Exhibit 1026, filed Apr. 30, 2013 in connection with IPR2012-00007: Illumina's Answer to Amended Complaint from The Trustees of Columbia University in the *City of New York* v. *Illumina, Inc.*, D. Del C.A. No. 12-376 (GMS), filed Dec. 21, 2012.
Exhibit 1029, filed Jun. 18, 2013 in connection with IPR2012-00007: U.S. Pat. No. 4,772,691, issued Sep. 20, 1988 to Herman.
Exhibit 1030, filed Jun. 18, 2013 in connection with IPR2012-00007: Rosenblum et al., "New Dye-Labeled Terminators for Improved DNA Sequencing Patterns," Nucleic Acid Research, 1997, vol. 25, No. 22, pp. 4500-4504.
Exhibit 1031, filed Jun. 18, 2013 in connection with IPR2012-00007: PCT International Publication No. WO 99/49082, published Sep. 30, 1999 to Invitrogen Corporation.
Exhibit 1032, filed Jun. 18, 2013 in connection with IPR2012-00007: U.S. Pat. No. 5,449,767, issued Sep. 12, 1995 to Ward et al.
Exhibit 1033, filed Jun. 18, 2013 in connection with IPR2012-00007: U.S. Pat. No. 5,948,648, issued Sep. 7, 1999 to Khan et al.
Exhibit 1034, filed Jun. 18, 2013 in connection with IPR2012-00007: Jun. 8, 2013 Videotaped Deposition Transcript of George M. Weinstock, Ph.D.

Exhibit 1036, filed Sep. 27, 2013 in connection with IPR2012-00007: "Next Generation Genomics: World Map of High-throughput Sequencers," Sep. 1, 2013.
Exhibit 1037, filed Sep. 27, 2013 in connection with IPR2012-00007: GB Application No. 2001 0029012, filed Dec. 4, 2001 by Balasubramanian et al.
Exhibit 1039, filed Sep. 27, 2013 in connection with IPR2012-00007: Videotaped Deposition Transcript of Dr. Xiaohai Liu, Mar. 20, 2013.
Exhibit 1040, filed Sep. 27, 2013 in connection with IPR2012-00007: Excerpt from videotaped Deposition Transcript of George M. Weinstock, Ph.D., Jun. 8, 2013.
Exhibit 1041, filed Sep. 27, 2013 in connection with IPR2012-00007: Seela et al., "Oligonucleotide Duplex Stability Controlled by the 7-Substituents of 7-Deazaguanine Bases," Bioorganic & Medical Chemistry Letters, vol. 5, No. 24, pp. 3049-3052, 1995.
Exhibit 1042, filed Sep. 27, 2013 in connection with IPR2012-00007: Ramzaeva et al., "123. 7-Deazaguanine DNA: Oligonucleotides with Hydrophobic or Cationic Side Chains," Helvetica Chimica Acta, vol. 80, pp. 1809-1822, 1997.
Exhibit 1043, filed Sep. 27, 2013 in connection with IPR2012-00007: Ramzaeva et al., "88. 7-Substituted 7-Deaza-2'-deoxyguanosines: Regioselective Halogenation of Pyrrolo[2,3-d]pyrimidine Nucleosides," Helvetica Chimica Acta, vol. 78, pp. 1083-1090, 1995.
Exhibit 1044, filed Sep. 27, 2013 in connection with IPR2012-00007: Seela et al., "Duplex Stability of Oligonucleotides Containing 7-Substituted 7-Deaza-and 8-Aza-7-Deazapurine Nucleosides," Nucleosides & Nucleotides, 16(7-9), pp. 963-966, 1997.
Exhibit 1045, filed Sep. 27, 2013 in connection with IPR2012-00007: Burgess et al., "Syntheses of Nucleosides Designed for Combinatorial DNA Sequencing," Chemistry—A European Journal, vol. 5, No. 3, pp. 951-960, 1999.
Exhibit 1046, filed Sep. 27, 2013 in connection with IPR2012-00007: U.S. Pat. No. 5,151,507, issued Sep. 29, 1992 to Hobbs, Jr. et al.
Exhibit 1047, filed Sep. 27, 2013 in connection with IPR2012-00007: U.S. Pat. No. 7,078,499, issued Jul. 18, 2006 to Odedra et al.
Exhibit 1048, filed Sep. 27, 2013 in connection with IPR2012-00007: GB Application No. 2000 0013276, filed Jun. 1, 2000 by Odedra et al.
Exhibit 1049, filed Sep. 27, 2013 in connection with IPR2012-00007: Jan. 28, 2013 Declaration of Dr. Bruce P. Branchaud in Support of Petition for Inter Partes Review of U.S. Pat. No. 7,057,026.
Exhibit 1050, filed Sep. 27, 2013 in connection with IPR2012-00007: Lee et al., "DNA sequencing with dye-labeled terminators and T7 DNA polymerase: effect of dyes and dNTPs on incorporation of dye-terminators and probability analysis of termination fragments," Nucleic Acids Research, vol. 20, No. 10, pp. 2471-2483, 1992.
Exhibit 1051, filed Sep. 27, 2013 in connection with IPR2012-00007: http://www.answers.com/topic/incubate, Accessed Sep. 27, 2013.
Exhibit 1052, filed Sep. 27, 2013 in connection with IPR2012-00007: http://en.wikipedia.org/wiki/Fluorenylmethyloxycarbonyl_chloride, Accessed Sep. 27, 2013.
Exhibit 1053, filed Sep. 27, 2013 in connection with IPR2012-00007: Sep. 27, 2013 Declaration of Kevin Burgess.
Exhibit 1054, filed Sep. 27, 2013 in connection with IPR2012-00007: Fuji, et al., "An Improved Method for Methoxymethylation of Alcohols under Mild Acidic Conditions," Synthesis—The Journal of Synthetic Organic Chemistry, pp. 276-277, Apr. 1975.
Exhibit 2001, filed Dec. 21, 2012 in connection with IPR2012-00007: Composition of a Nucleotide.
Exhibit 2006, filed Jun. 25, 2013 in connection with IPR2012-00007: Dower patent with highlights.
Exhibit 2010, filed Jun. 24, 2013 in connection with IPR2012-00007: U.S. Pat. No. 8,088,575 (filed Jul. 19, 2010, issued Jan. 3, 2012) (Exhibit 1001 in IPR2013-00011).
Exhibit 2011, filed Jun. 24, 2013 in connection with IPR2012-00007: U.S. Pat. No. 7,713,698 (filed Aug. 20, 2007, issued May 11, 2010) (Exhibit 1001 in IPR2012-00006).
Exhibit 2012, filed Jun. 24, 2013 in connection with IPR2012-00007: U.S. Pat. No. 7,790,869 (filed Jun. 5, 2007, issued Sep. 7, 2010) (Exhibit 1001 in IPR2012-00007).
Exhibit 2013, filed Jun. 24, 2013 in connection with IPR2012-00007: Oct. 2, 2012 Declaration of George Weinstock Under 37 CFR 1.132 (Exhibit 1021 in IPR2013-00011).

(56) References Cited

OTHER PUBLICATIONS

Exhibit 2014, filed Jun. 24, 2013 in connection with IPR2012-00007: Petition for Inter Partes Review of U.S. Pat. No. 8,088,575 (Paper 4 in IPR2013-00011).
Exhibit 2015, filed Jun. 24, 2013 in connection with IPR2012-00007: Metzker et al. (1994) Termination of DNA synthesis by novel 3'-modified-deoxyribonucleoside 5'-triphosphates. Nucleic Acids Res. 22:4259-4267.
Exhibit 2016, filed Jun. 24, 2013 in connection with IPR2012-00007: Wu et al. (2007) Termination of DNA synthesis by N6-alkylated, not 3'-O-alkylated, photocleavable 2'-deoxyadenosine triphosphates. Nucleic Acids Res. 35:6339-6349.
Exhibit 2017, filed Jun. 24, 2013 in connection with IPR2012-00007: Sep. 15, 2012 Declaration of George Weinstock Under 37 CFR 1.132 (Exhibit 1021 in IPR2012-00007).
Exhibit 2018, filed Jun. 24, 2013 in connection with IPR2012-00007: Sep. 15, 2012 Declaration of George Weinstock Under 37 CFR 1.132 (Exhibit 1021 in IPR2012-00006).
Exhibit 2019, filed Jun. 24, 2013 in connection with IPR2012-00007: Definition of "DNA microarray." http://en/wikipedia.org/wiki/DNA_microarray.
Exhibit 2020, filed Jun. 24, 2013 in connection with IPR2012-00007: Brettin et al. (2005) Expression capable library for studies of *Neisseria gonorrhoeae*, version 1.0 BMC Microbiology. 5:50.
Exhibit 2021, filed Jun. 24, 2013 in connection with IPR2012-00007: George M. Weinstock, Handbook of Molecular Microbial Ecology, vol. 1—Chapter 18: The Impact of Next-Generation Sequencing Technologies on Metagenomics 141-147 Frans J. de Bruijn ed., John Wiley & Sons, Inc. (2011).
Exhibit 2022, filed Jun. 24, 2013 in connection with IPR2012-00007: Sep. 16, 2012 Petition for Inter Partes Review of U.S. Pat. No. 7,713,698 (Paper 3 in IPR2012-00006).
Exhibit 2023, filed Jun. 24, 2013 in connection with IPR2012-00007: Sep. 16, 2012 Petition for Inter Partes Review of U.S. Pat. No. 7,790,869 (Paper 5 in IPR2012-00007).
Exhibit 2024, filed Jun. 24, 2013 in connection with IPR2012-00007: Maxam and Gilbert (1977) A new method for sequencing DNA, Proc. Natl. Acad. Sci. USA. 74:560-564.
Exhibit 2025, filed Jun. 24, 2013 in connection with IPR2012-00007: Sanger et al. (1977) DNA sequencing with chain-terminating inhibitors, Proc. Natl. Acad. Sci. USA. 74:5463-5467.
Exhibit 2026, filed Jun. 24, 2013 in connection with IPR2012-00007: Pennisi (2000) DOE Team Sequences Three Chromosomes, Science. 288:417-419.
Exhibit 2027, filed Jun. 24, 2013 in connection with IPR2012-00007: Welch and Burgess (1999) Synthesis of Fluorescent, Photolabile 3'-O-Protected nucleoside Triphosphates for the Base Addition Sequencing Scheme, nucleosides & Nucleotides. 18:197-201.
Exhibit 2028, filed Jun. 24, 2013 in connection with IPR2012-00007: Hyman (1998) A New Method of Sequencing DNA, Analytical Biochemistry 174:423-436.
Exhibit 2029, filed Jun. 24, 2013 in connection with IPR2012-00007: U.S. Pat. No. 5,302,509 (filed Feb. 27, 1991, issued Apr. 12, 1994).
Exhibit 2030, filed Jun. 24, 2013 in connection with IPR2012-00007: Canard and Sarfati (1994) DNA polymerase fluorescent substrates with reversible 3'-tags, Gene. 1481-6.
Exhibit 2031, filed Jun. 24, 2013 in connection with IPR2012-00007: U.S. Pat. No. 8,399,188 (filed Sep. 4, 2007, issued Mar. 19, 2013).
Exhibit 2032, filed Jun. 24, 2013 in connection with IPR2012-00007: Sarfati et al. (1987) Synthesis of Fluorescent or Biotinylated Nucleoside Compounds, Tetrahedron Letters. 43:3491-3497.
Exhibit 2033, filed Aug. 30, 2013 in connection with IPR2012-00007: Jun. 25, 2013 Substitute Declaration of Dr. George L. Trainor [redacted].
Exhibit 2034, filed Jun. 25, 2013 in connection with IPR2012-00007: Jingyue Ju et. al. (2006) Four-color DNA sequencing by synthesis using cleavable fluorescent nucleotide reversible terminators, Proceedings of the National Academy of Sciences. 103: 19635-19640.
Exhibit 2035, filed Jun. 25, 2013 in connection with IPR2012-00007: Batista et al. (2008) PRG-1 and 21U-RNAs Interact to Form the piRNA Complex Required for Fertility in *C. elegans*. Molecular Cell 31:1-12.
Exhibit 2036, filed Jun. 25, 2013 in connection with IPR2012-00007: Form 7 Review Context and Analysis, Biomedical Engineering and Research to Aid Persons with Disabilities Programs Dec. 19-20, 2000 Panel Review, Fluorescence Imaging Chip System for Massive Parallel DNA Sequencing. Proposal No. BES-0097793.
Exhibit 2037, filed Jun. 25, 2013 in connection with IPR2012-00007: Oct. 1, 2006 Request for opinion on manuscript by J. Ju et. al., Proceedings of National Academy of Sciences, U.S.A.
Exhibit 2038, filed Jun. 25, 2013 in connection with IPR2012-00007: Correspondence between George Rupp, Chancellor, Columbia University and Richard T. Schlossberg, President, The David and Lucile Packard Foundation (2001).
Exhibit 2039, filed Jun. 25, 2013 in connection with IPR2012-00007: The David and Lucile Packard Foundation, Packard Fellowships for Science and Engineering, http://www.packard.org/what-wefund/conservation-and-science/packard-fellowships-for-science-andengineering/ (last visited Jun. 25, 2013).
Exhibit 2040, filed Jun. 26, 2013 in connection with IPR2012-00007: "Chemistry for Next-Generation Sequencing." http://www.illumina.com/technology/sequencing_technology.ilmn.
Exhibit 2041, filed Jun. 26, 2013 in connection with IPR2012-00007: Chiang et al. (2010) Mammalian microRNAs: experimental evaluation of novel and previously annotated genes, Genes & Dev. 24:992, 993.
Exhibit 2042, filed Jun. 26, 2013 in connection with IPR2012-00007: Seo et al. (2004) Photocleavable fluorescent nucleotides for DNA sequencing on a chip constructed by site-specific coupling chemistry, Proc. Natl Acad. Sci. 101(15):5488-5493.
Exhibit 2043, filed Jun. 26, 2013 in connection with IPR2012-00007: Curriculum vitae of Mr. Raymond S. Sims.
Exhibit 2044, filed Jun. 26, 2013 in connection with IPR2012-00007: Prior Testimony of Mr. Raymond S. Sims.
Exhibit 2045, filed Jun. 26, 2013 in connection with IPR2012-00007: Documents reviewed by Mr. Raymond S. Sims in this Proceeding.
Exhibit 2052, filed Jun. 26, 2013 in connection with IPR2012-00007: Gary Schroth Proof of Chiang Paper.
Exhibit 2074, filed Jun. 26, 2013 in connection with IPR2012-00007: Information about Dr. Ju's intellectual property sent to Illumina.
Exhibit 2090, filed Jun. 26, 2013 in connection with IPR2012-00007: IPR Default Protective Order.
Exhibit 2091, filed Jun. 26, 2013 in connection with IPR2012-00007: Declaration of Raymond S. Sims.
Exhibit 2092, filed Oct. 1, 2013 in connection with IPR2012-00007: Rough transcript of the Sep. 4, 2013 deposition of Dr. George L. Trainor.
Exhibit 2093, filed Oct. 1, 2013 in connection with IPR2012-00007: Excerpt from Protective Groups in Organic Synthesis, 3rd Ed. (Theodora W. Greene and Peter G.M. Wuts ed., John Wiley & Sons, Inc. 1999).
Exhibit 2094, filed Oct. 1, 2013 in connection with IPR2012-00007: Final transcript of the Sep. 4-6, 2013 deposition of Dr. George L. Trainor.
Exhibit 2095, filed Oct. 1, 2013 in connection with IPR2012-00007: Final transcript of the Sep. 3, 2013 deposition of Raymond S. Sims.
Record of Dec. 17, 2013 Oral Hearing, entered Feb. 10, 2014 in connection with IPR2012-00006, IPR2012-00007, and IPR2013-00011.
Mar. 6, 2014 Final Written Decision in connection with IPR2012-00006.
Mar. 6, 2014 Final Written Decision in connection with IPR2012-00007.
Mar. 6, 2014 Final Written Decision in connection with IPR2013-00011.
U.S. Appl. No. 13/959,660, filed Aug. 5, 2013, Ju et al.
U.S. Appl. No. 14/119,846, filed Nov. 22, 2013, Ju et al.
U.S. Appl. No. 14/242,487, filed Apr. 1, 2014, Ju et al.
Pending claims in U.S. Appl. No. 12/084,457, filed Apr. 30, 2008 by Ju et al. (published as 2009/0263791 A1, Oct. 22, 2009).

(56) References Cited

OTHER PUBLICATIONS

Pending claims in U.S. Appl. No. 13/186,353, filed Jul. 19, 2011 by Ju et al (published as 2012/0156680 A1, Jun. 21, 2012).
Pending claims in U.S. Appl. No. 13/959,660.
Benson, S.C., Mathies, R.A., and Glazer, A.N. (1993) Heterodimeric DNA-binding dyes designed for energy transfer: stability and applications of the DNA complexes. Nucleic Acids Res. 21:5720-5726.
Benson, S.C., Singh, P., and Glazer, A.N. (1993) Heterodimeric DNA-binding dyes designed for energy transfer: synthesis and spectroscopic properties. Nucleic Acids Res. 21:5727-5735.
Chen, X. and Kwok, P.-Y. (1997) Template-directed dye-terminator incorporation (TDI) assay: a homogeneous DNA, diagnostic method based on fluorescence resonance energy transfer. Nucleic Acids Res. 25:347-353.
Edwards, J. et al. (2001) DNA sequencing using biotinylated dideoxynucleotides and mass spectrometry. Nucleic Acids Res. 29(21) 1041-1046.
Griffin, T.J. et al. (1999) Direct Genetic Analysis by Matrix-Assisted Laser Desorption/Ionization Mass Spectrometry. Proc. Nat. Acad. Sci. USA 96:6301-6306.
Hacia J.G., Edgemon K., Sun B., Stern D., Fodor S.A., and Collins F.S. (1998) Two Color Hybridization Analysis Using High Density Oligonucleotide Arrays and Energy Transfer Dyes. Nucleic Acids Res. 26:3865-6.
Haff L.A., et al. (1997) Multiplex Genotyping of PCR Products with Mass Tag-Labeled Primers. Nucleic Acids Res. 25(18):3749-3750.
Jiang-Baucom, P. et al. (1997) DNA Typing of Human Leukocyte Antigen Sequence Polymorphisms by Peptide Nucleic Acid Probes and MALDI-TOF Mass Spectrometry. Anal. Chem. 69:4894-4896.
Jingyue Ju, et al. (1996) Cassette labeling for facile construction of energy transfer fluorescent primers. Nuc. Acids Res. 24(6):1144-1148.
Ju J., Glazer, A.N., and Mathies, R.A. (1996) Energy transfer primers: A new fluorescence labeling paradigm for DNA sequencing and analysis. Nature Medicine 2: 246-249.
Ju J., Ruan C., Fuller, C.W., Glazer, A.N., and Mathies, R.A. (1995) Fluorescence energy transfer dye-labeled primers for DNA sequencing and analysis. Proc. Natl. Acad. Sci. USA 92: 4347-4351.
Li, J., (1999) Single Oligonucleotide Polymorphism Determination Using Primer Extension and Time-of-Flight Mass Spectrometry. Electrophoresis, 20:1258-1265.
Lyamichev, A. et al. (1999) Polymorphism Identification and Quantitative Detection of Genomic DNA by Invasive Cleavage of Oligonucleotide Probes. Nat. Biotech. 17:292-296.
Ross, P. et al. (1998) High Level Multiplex Genotyping by MALDI-TOF Mass Spectrometry. Nat. Biotech. 16:1347-1351.
Ross, P.L. et al. (1997) Discrimination of Single-Nucleotide Polymorphisms in Human DNA Using Peptide Nucleic Acid Probes Detected by MALDI-TOF Mass Spectrometry. Anal. Chem. 69:4197-4202.
Speicher, M.R., Ballard, S.G., and Ward, D.C. (1996) Karyotyping human chromosomes by combinatorial multi-fluor FISH. Nature Genetics 12: 368-375.
Stoerker, J., et al. (2000) Rapid Genotyping by MALDI-monitored nuclease selection from probe libraries. Nat. Biotech. 18:1213-1216.
Tang, K., Fu, D.J., Julien, D., Braun, A., Cantor, C.R., and Koster, H. (1999) Chip-based genotyping by mass spectrometry. Proc. Natl. Acad. Sci. USA. 96:10016-10020.
Tong, X. and Smith, L.M. (1992) Solid-Phase Method for the Purification of DNA Sequencing Reactions. Anal. Chem. 64:2672-2677.
Arbo, et al. (1993) Solid Phase Synthesis of Protected Peptides Using New Cobalt (III) Amine Linkers, Int. J. Peptide Protein Res. 42:138-154.
Bergseid M., Baytan A.R., Wiley J.P., Ankener W.M., Stolowitz, Hughs K.A., Chestnut J.D., Small-molecule base chemical affinity system for the purification of proteins. BioTechniques 29:1126-1133 (2000).

Chiu, N.H., Tang, K., Yip, P., Braun, A., Koster, H., and Cantor, C.R. (2000) Mass spectrometry of single-stranded restriction fragments captured by an undigested complementary sequence. Nucleic Acids Res. 28:E31.
Fei, Z. et al. (1998) MALDI-TOF mass spectrometric typing of single nucleotide polymorphisms with mass-tagged ddNTPs. Nucleic Acids Research 26(11):2827-2828.
Fu, D.J., Tang, K., Braun, A., Reuter, D., Darnhofer-Demar, B., Little, D.P., O'Donnell, M.J., Cantor, C.R., and Koster, H. (1998) Sequencing exons 5 to 8 of the p53 gene by MALDI-TOF mass spectrometry. Nat. Biotechnol. 16:381-384.
Jurinke, C., van de Boom, D., Collazo, V., Luchow, A., Jacob, A., and Koster H. (1997) Recovery of nucleic acids from immobilized biotin-streptavidin complexes using ammonium hydroxide and application in MALDI-TOF mass spectrometry. Anal. Chem. 69:904-910.
Monforte, J.A. and Becker, C.H., (1997) High-throughput DNA analysis by time-of-flight mass spectrometry. Nat. Med. 3(3):360-362.
Roskey, M.T, Juhasz, P., Smirnov, I.P., Takach, E.J., Martin, S.A., and Haff, L.A. (1996) DNA sequencing by delayed extraction-matrix-assisted laser desorption/ionization time of flight mass spectrometry. Proc. Natl. Acad. Sci. USA. 93:4724-4729.
Axelrod VD, et al (1978) "Specific termination of RNA polymerase synthesis as a method of RNA and DNA sequencing". Nucleic Acids Res. 5(10): 3549 3563.
Saxon E and Bertozzi CR (2000) "Cell surface engineering by a modified Staudinger reaction". Science 287: 2007 2010.
Canard B, et al. (1995) "Catalytic editing properties of DNA polymerases". Proc. Natl. Acad. Sci. USA 92: 10859 10863.
Caruthers MH. (1985) "Gene synthesis machines: DNA chemistry and its uses". Science 230: 281 285.
Chee M, et al. (1996) "Accessing genetic information with high density DNA arrays". Science. 274: 610 614.
Hyman ED, (1988) "A new method of sequencing DNA". Analytical Biochemistry 174: 423 436.
Ireland RE, Varney MD (1986) "Approach to the total synthesis of chlorothricolide synthesis of (+/-)-19.20-dihydro-24-O-methylchlorothricolide, methyl ester, ethyl carbonate". J. Org. Chem. 51: 635 648.
Kamal A, Laxman E, Rao NV. (1999) "A mild and rapid regeneration of alcohols from their allylic ethers by chlorotrimethylsilane/sodium iodide". Tetrahedron Lett 40: 371 372.
Lee LG, et al. (1992) "DNA sequencing with dye labeled terminators and T7 DNA polymerase effect of dyes and dNTPs on incorporation of dye terminators and probability analysis of termination fragments". Nucleic Acids Res. 20: 2471 2483.
Lee LG, et al, (1997) "New energy transfer dyes for DNA sequencing". Nucleic Acids Res. 25: 2816 2822.
Metzker ML, Raghavachari R, Richards S, Jacutin SE, Civitello A, Burgess K, Gibbs RA. (1994) "Termination of DNA synthesis by novel 3' modified deoxyribonucleoside 5' triphosphates". Nucleic Acids Res. 22: 4259 4267.
Olejnik J, Ludemann HC, Krzymanska Olejnik E, Berkenkamp S, Hillenkamp F, Rothschild KJ. (1999) "Photocleavable peptide DNA conjugates: synthesis and applications to DNA analysis using MALDI MS". Nucleic Acids Res. 27: 4626 4631.
Olejnik J, Sonar S, Krzymanska-Olejnik E, Rothschild KJ. (1995) "Photocleavable biotin derivatives: a versatile approach for the isolation of biomolecules". Proc. Natl. Acad. Sci. USA. 92: 7590-7594.
Pelletier H, Sawaya MR, Kumar A, Wilson SH, Kraut J. (1994) "Structures of ternary complexes of rat DNA polymerase β, a DNA template-primer, and ddCTP". Science 264: 1891-1903.
Prober JM, Trainor GL, Dam RJ, Hobbs FW, Robertson CW, Zagursky RJ, Cocuzza AJ, Jensen MA, Baumeister K. (1987) "A system for rapid DNA sequencing with fluorescent chain-terminating dideoxynucleotides". Science 238: 336-341.
Ronaghi M, Uhlen M, Nyren P. (1998) "A sequencing Method based on real-time pyrophosphate". Science 281: 364-365.
Rosenblum, B.B. et al. (1997) "New dye-labeled terminators for improved DNA sequencing patterns". Nucleic Acids Res. 25: 4500-4504.

(56) References Cited

OTHER PUBLICATIONS

Schena M, Shalon D, Davis, R. Brown P.O. (1995) "Quantitative monitoring of gene expression patterns with a cDNA microarray". Science 270: 467-470.
Welch MB, Burgess K, (1999) "Synthesis of fluorescent, photolabile 3'-O-protected nucleoside triphosphates for the base addition sequencing scheme". Nucleosides and Nucleotides 18:197-201.
Badman, E. R. et al., "A Parallel Miniature Cylindrical Ion Trap Array," Anal. Chem. (2000) 72:3291-3297.
Badman, E. R. et al., "Cylindrical Ion Trap Array with Mass Selection by Variation in Trap Dimensions," Anal. Chem. (2000) 72:5079-5086.
Burgess, K. et al., "Photolytic Mass Laddering for Fast Characterization of Oligomers on Single Resin Beads," J. Org. Chem. (1997) 62:5662-5663.
Liu, H. et al., "Development of Multichannel Devices with an Array of Electrospray Tips for High-Throughput Mass Spectrometry," Anal. Chem. (2000) 72:3303-3310.
Woolley, A. T. et al., "High-Speed DNA Genotyping Using Microfabricated Capillary Array Electrophoresis Chips," Anal. Chem. (1997) 69:2181-2186.
Hultman et al., "Direct Solid Phase Sequencing of Genomic and Plasmid DNA Using Magnetic Beads as Solid Support", Nucleic Acids Research, 17(3):4937-4946.
Buschmann et al. (1999), The Complex Formation of α, ω-Dicarboxylic Acids and α, ω-Diols with Cucurbituril and α-Cyclodextrin, Acta Chim. Slov. 46(3):405-411.
Kolb et al. (2001), Click Chemistry: Diverse Chemical Function From a Few Good Reactions, Angew. Chem. Int. Ed. 40:2004-2021.
Seo T., et al., (2003) J. Org. Chem. 68:609-612.
Ikeda, K. et al. "A Non-Radioactive DNA Sequencing Method Using Biotinylated Dideoxynucleoside Triphosphates and Delta TTH DNA Polymerase" DNA Research, 2(31):225-227 (1995).
Kim Sobin et al. "Solid Phase Capturable Dideoxynucleotides for Multiplex Genotyping Using Mass Spectrometry" Nucleic Acids Research, 30(16):e85.1-e85.6, (2002).
Wendy S Jen, John J.M. Wiener, and David W.C. MacMillan "New Strategies for Organic Catalysis: The First Enantioselective Orgacnocatalytic 1,3-Dipolar Cycloaddition" J. Am. Chem. Soc. 2000, 122, 9874-9875.
Supplementary European Search Report issued Feb. 16, 2004 in connection with European Patent Application No. 01 97 7533.
Supplementary European Search Report issued Feb. 9, 2007 in connection with European Patent Application No. 03 76 4568.6.
Supplementary European Search Report issued May 25, 2005 in connection with European Patent Application No. 02 72 8606.1.
Supplementary European Search Report issued Jun. 7, 2005 in connection with European Patent Application No. 01 96 8905.
International Preliminary Examination Report issued on Mar. 18, 2005 in connection with PCT/US03/21818.
International Preliminary Examination Report issued on Apr. 3, 2003 in connection with PCT/US01/31243.
International Preliminary Examination Report issued on Feb. 25, 2003 in connection with PCT/US01/28967.
International Preliminary Examination Report issued on Mar. 17, 2003 in connection with PCT/US02/09752.
International Preliminary Report on Patentability issued on Sep. 5, 2006 in connection with PCT/US05/006960.
International Search Report issued May 13, 2002 in connection with PCT/US01/31243.
International Search Report issued Jan. 23, 2002 in connection with PCT/US01/28967.
International Search Report issued Sep. 18, 2002 in connection with PCT/US02/09752.
International Search Report issued Sep. 26, 2003 in connection with PCT/US03/21818.
International Search Report issued Jun. 8, 2004 in connection with PCT/US03/39354.
International Search Report issued Nov. 4, 2005 in connection with PCT/US05/06960.
International Search Report issued Dec. 15, 2006 in connection with PCT/US05/13883.
Written Opinion of the International Searching Authority issued Oct. 27, 2005 in connection with PCT/US05/06960.
Written Opinion of the International Searching Authority issued Dec. 15, 2006 in connection with PCT/US05/13883.
Lewis et al. (2002), Click Chemistry in Situ: Acetylcholinesterase as a Reaction Vessel for the Selective Assembly of a Femtomolar Inhibitor from an Array of Building Blocks, Angew. Chem. Int. Ed., 41(6):1053-1057.
Fallahpour R., (2000) Helvetica Chimica Acta. 83:384-393.
Kim et al. (2003), Multiplex genotyping of the human β2-adrenergic receptor gene using solid-phase capturable dideoxynucleotides and mass spectronomy, Analytical Biochem., 316:251-258.
Kokoris et al. (2000), High-throughput SNP genotyping with the masscode system, Molecular Diagnosis, 5(4):329-340.
Leroy et al. (2000), Diagnosis of ebola haemorrhagic fever RT-PCR in an Epidemic setting, Jour. of Medic. Virol., 60:463-467.
Häfliger et al. (1997), Seminested RT-PCR systems for small round structured viruses and detection of enteric viruses in seafood, Int. Jour. of Food Micro., 37:27-36.
Buck et al. (1999), Design strategies and performance of custom DNA sequencing primers, Biotechniques, 27:528-536.
Elango et al. (1983), Amino acid sequence of human respiratory syncytial virus nucleocapsid protein, Nucleic Acids Research, 11(17):5941-5951.
Extended European Search Report issued Jul. 18, 2007 in connection with European Patent Application No. 07004522.4.
Partial European Search Report issued Apr. 26, 2007 in connection with European Patent Application No. 07004522.4.
Kraevskii, A.A. et al., (1987), Substrate Inhibitors of DNA Biosynthesis, Molecular Biology, 21:25-29.
Henner, W.D. et al., (1983), Enzyme Action at 3' Termini of Ionizing Radiation-Induced DNA Strand Breaks, J. Biol. Chem. 258(24):15198-15205.
Office Action issued Oct. 25, 2002 in connection with U.S. Appl. No. 09/972,364.
Office Action issued Mar. 14, 2003 in connection with U.S. Appl. No. 09/972,364.
Office Action issued Aug. 10, 2007 in connection with U.S. Appl. No. 11/119,231.
Office Action issued Sep. 21, 2007 in connection with U.S. Appl. No. 10/380,256.
Notice of Allowance issued Sep. 6, 2007 in connection with U.S. Appl. No. 10/702,203.
Restriction Requirement issued in connection with U.S. Appl. No. 10/521,206.
Office Action issued Nov. 14, 2007 in connection with U.S. Appl. No. 10/735,081.
Official Action issued May 21, 2007 in connection with European Patent Application No. 01968905.8.
Official Action issued Mar. 31, 2006 in connection with European Patent Application No. 01968905.8.
Tuncel et al. (1999) Catalytically Self-Threading Polyrotaxanes, Chem. Comm. 1509-1510.
Notification of Transmittal of International Search Report and Written Opinion, issued Nov. 23, 2007.
Meng et al., (2006), Design and Synthesis of a Photocleavable Fluorescent Nucleotide 3'-O-Allyl-dGTP-PC-Biodipy-FL-510 as a Reversible Terminator for DNA Sequencing by Synthesis, J. Org. Chem 71:3248-3252.
Li et al., (2003), A photocleavable Fluorescent Nucleotide for DNA Sequencing and Analysis, PNAS, 100(2):414-419.
Seo et al., (2004), Photocleavable Fluorescent Nucleotides for DNA Sequencing on a Chip Constructed by Site-Specific Coupling Chemistry, PNAS 101(15):5488-5493.
Seo et al., (2004), Four-Color DNA Sequencing by Synthesis on a Chip Using Photocleavable Fluorescent Nucleotides, PNAS 102(17):5926-5931.
Ruparel et al., (2005), Design and Synthesis of a 3'-O- Allyl Photocleavable Fluorescent Nucleotide as a Reversible Terminator for DNA Sequencing by Synthesis, PNAS, 102(17):5932-5937.

(56) References Cited

OTHER PUBLICATIONS

International Search Report issued Oct. 29, 2007 in connection with PCT International Application No. PCT/US07/13559.
U.S. Appl. No. 11/894,808, filed Aug. 20, 2007.
U.S. Appl. No. 11/894,690, filed Aug. 20, 2007.
U.S. Appl. No. 11/810,509, filed Jun. 5, 2007.
U.S. Appl. No. 09/684,670, filed Oct. 6, 2000, Ju et al.
Nickel W, et al. (1992) "Interactions of azidothymidine triphosphate with the cellular DNA polymerases alpha, delta, and epsilon and with DNA primase". Journal of Biological Chemistry. 267(2):848-854.
PCT International Publication No. WO 08/069973 A2 Ju et al., published Jun. 12, 2008.
Official Action issued Mar. 14, 2008 in connection with European Patent Application No. 07004522.4.
Office Action issued Jun. 24, 2008 in connection with U.S. Appl. No. 11/894,690.
Office Action issued Jul. 8, 2008 in connection with U.S. Appl. No. 10/591,520.
Notification of Transmittal of International Search Report and Written Opinion, issued Feb. 6, 2008 in connection with International Application No. PCT/US06/42739.
Notification Concerning Transmittal of International Preliminary Report on Patentability (Including Written Opinion of the International Searching Authority) issued May 15, 2008 in connection with PCT/US2006/042698.
Notification of Transmittal the International Search Report and Written Opinion, issued May 22, 2008 in connection with International Application No. PCT/US06/45180.
Notification of Transmittal the International Search Report and Written Opinion, issued Aug. 16, 2008 in connection with International Application No. PCT/US07/24646.
Bai et al. (2003) "Photocleavage of a 2-nitrobenzyl linker bridgina a fluorophore to the 5' end of DNA," PNAS, vol. 100, No. 2, pp. 409-413.
Nielsen et al. (2004) "Multiplexed sandwich assays in microarray format," Journal of Immunological Methods, vol. 290, pp. 107-120.
Zhang et al. (2002) "Synthesis of Releasable Electrophore Tags for Applications in Mass Spectrometry," Bioconjugate Chem, vol. 13, pp. 1002-1012.
Sep. 3, 2008 Office Action issued in connection with U.S. Appl. No. 11/894,808.
Notification of Transmittal the International Search Report and Written Opinion, issued Sep. 9, 2008 in connection with International Application No. PCT/US06/24157.
Hanshaw et al. (2004) "An Indicator displacement system for fluorescent detection of phosphate oxyanions under physiological conditions" Tetrahedron Letters, vol. 45, pp. 8721-8724.
U.S. Appl. No. 12/084,338 filed Apr. 28, 2008.
U.S. Appl. No. 12/085,343, filed May 19, 2008.
Oct. 3, 2012 Petition for Inter Partes Review of U.S. Pat. No. 8,088,575.
Oct. 3, 2012 Motion to Waive Page Limit and Proposed Petition in connection with Petition for Inter Partes Review of U.S. Pat. No. 8,088,575.
Jan. 7, 2013 Preliminary Response under 37 C.F.R. 42.107 in connection with IPR2013-00011.
Mar. 12, 2013 Decision on Petition for Inter Partes Review in connection with IPR2013-00011.
Mar. 26, 2013 Request for Reconsideration in connection with IPR2013-00011.
Mar. 26, 2013 Request for Rehearing under 37 C.F.R. 42.71 of Decision to Institute Inter Partes Review in connection with IPR2013-00011.
Apr. 26, 2013 Opposition to Request for Reconsideration (Rehearing) Under 37 C.F.R. 42.71.(C) in connection with IPR2013-00011.
May 10, 2013 Decision on Request for Rehearing in connection IPR2013-00011.
Jun. 25, 2013 Motion to Amend Under 37 C.F.R. 42.121 in connection with IPR2013-00011.
Aug. 30, 2013 Substitute Patent Owner Response Under 37 C.F.R. 42.120 in connection with IPR2013-00011.
Sep. 27, 2013 Petitioner Opposition to Motion to Amend in connection with IPR2013-00011.
Sep. 27, 2013 Petitioner Reply to Response to Petition in connection with IPR2013-00011.
Oct. 28, 2013 Patent Owner Reply on Motion to Amend in connection with IPR2013-00011.
Exhibit 1001, filed Oct. 3, 2012 in connection with IPR2013-00011: U.S. Pat. No. 8,088,575 issued Jan. 3, 2012 to Ju et al.
Exhibit 1002, filed Oct. 3, 2012 in connection with IPR2013-00011: PCT International Application No. PCT/US90/06678 filed Oct. 26, 1990, published on May 16, 1991 as Publication No. WO 91/06678 to SRI International.
Exhibit 1003, filed Oct. 3, 2012 in connection with IPR2013-00011: Prober et al. (1987), "A System for Rapid DNA Sequencing with Fluorescent Chain-Terminating Dideoxynucleotides", *Science* vol. 238, Oct. 16, 1987, pp. 336-341.
Exhibit 1004, filed Oct. 3, 2012 in connection with IPR2013-00011: U.S. Pat. No. 5,242,796 issued Sep. 7, 1993 to Prober et al.
Exhibit 1005, filed Oct. 3, 2012 in connection with IPR2013-00011: U.S. Pat. No. 5,547,839 issued Aug. 20, 1996 to Dower et al.
Exhibit 1006, filed Oct. 3, 2012 in connection with IPR2013-00011: PCT International Application No. PCT/US96/02342 filed Feb. 21, 1996, published on Sep. 6, 1996 as Publication No. WO 96/27025 to Ely Rabani.
Exhibit 1007, filed Oct. 3, 2012 in connection with IPR2013-00011: PCT International Application No. PCT/GB00/00873 filed Mar. 10, 2000, published on Sep. 14, 2000 as Publication No. WO 00/53805 to ASM Scientific, Inc.
Exhibit 1008, filed Oct. 3, 2012 in connection with IPR2013-00011: U.S. Pat. No. 7,270,951 issued Sep. 18, 2007 to Stemple et al.
Exhibit 1009, filed Oct. 3, 2012 in connection with IPR2013-00011: U.S. Application for A Method for Direct Nucleic Acid Sequencing; U.S. App. No. 09/266,187, filed Mar. 10, 1999.
Exhibits 1010-1012, filed Oct. 3, 2012 in connection with IPR2013-00011: PCT International Application No. PCT/JP97/00239, filed Jan. 31, 1997, published on Aug. 6, 1998 as Publication No. WO 98/33939 to Hitachi, Ltd. with certified English translation, and Translation Affidavit.
Exhibit 1013, filed Oct. 3, 2012 in connection with IPR2013-00011: U.S. Pat. No. 5,047,519 issued Sep. 10, 1991 to Hobbs, Jr. et al.
Exhibit 1014, filed Oct. 3, 2012 in connection with IPR2013-00011: U.S. Pat. No. 4,804,748 issued Feb. 14, 1989 to Seela.
Exhibit 1015, filed Oct. 3, 2012 in connection with IRP2013-00011: U.S. Patent No. 5,844,106 issued Dec. 1, 1998 to Seela et al.
Exhibit 1016, filed Oct. 3, 2012 in connection with IPR2013-00011: PCT International Application No. PCT/US89/02170, filed May 18, 1989, published on Nov. 30, 1989 as Publication No. WO 89/11548 to Cetus Corporation.
Exhibit 1017, filed Oct. 3, 2012 in connection with IPR2013-00011: U.S. Pat. No. 7,037,687 issued May 2, 2006 to Williams et al.
Exhibit 1018, filed Oct. 3, 2012 in connection with IPR2013-00011: U.S. Pat. No. 6,255,083 issued Jul. 3, 2001 to Williams.
Exhibit 1019, filed Oct. 3, 2012 in connection with IPR2013-00011: U.S. Pat. No. 6,001,566 issued Dec. 14, 1999 to Canard et al.
Exhibit 1020, filed Oct. 3, 2012 in connection with IPR2013-00011: PCT international Application No. PCT/GB93/00848, filed Apr. 22, 1993, published on Oct. 28, 1993 as Publication No. WO 93/21340 to Medical Research Council.
Exhibit 1021, filed Oct. 3, 2012 in connection with IPR2013-00011: Oct. 3, 2012 Declaration of George Weinstock Under Rule 37 C.F.R. §1.132.
Exhibit 1022, filed Oct. 3, 2012 in connection with IPR2013-00011: Excerpts of File History of U.S. Pat. No. 8,038,575.
Exhibit 1025, filed Apr. 30, 2013 in connection with IPR2013-00011: Columbia's Amended Complaint from The Trustees of Columbia University in the *City of New York v. Illumina, Inc.*, D. Del C.A. No. 12-376 (GMS), filed Apr. 11, 2012.
Exhibit 1026 filed Apr. 30, 2013 in connection with IPR2013 -00011: Illumina's Answer to Amended Complaint from The Trustees of Columbia University in the *City of New York v. Illumina, Inc.*, D. Del C.A. No. 12-376 (GMS), filed Dec. 21, 2012.

(56) References Cited

OTHER PUBLICATIONS

Exhibit 1029, filed Jun. 18, 2013 in connection with IPR2013-00011: U.S. Pat. No. 4,772,691, issued Sep. 20, 1988 to Herman.
Exhibit 1030, filed Jun. 18, 2013 in connection with IPR2013-00011: Rosenblum et al., "New Dye-Labeled Terminators for Improved DNA Sequencing Patterns," Nucleic Acid Research, 1997, vol. 25, No. 22. pp. 4500-4504.
Exhibit 1031, filed Jun. 18, 2013 in connection with IPR2013-00011: PCT International Publication No. WO 99/49082, published Sep. 30, 1999 to Invitrogen Corporation.
Exhibit 1032, filed Jun. 18, 2013 in connection with IPR2013-00011: U.S. Pat. No. 5,449,767, issued Sep. 12, 1995 to Ward et al.
Exhibit 1033, filed Jun. 19, 2013 in connection with IPR2013-00011: U.S. Pat. No. 5,948,648, issued Sep. 7, 1999 to Khan et al.
Exhibit 1034, filed Jun. 18, 2013 in connection with IPR2013-00011: Jun. 8, 2013 Videotaped Deposition Transcript of George M. Weinstock, Ph.D.
Exhibit 1036, filed Sep. 27, 2013 in connection with IPR2013-00011: "Next Generation Genomics: World Map of High-throughput Sequencers," Sep. 1, 2013.
Exhibit 1037, filed Sep. 27, 2013 in connection with IPR2013-00011: GB Application No. 2001 0029012, filed Dec. 4, 2001 by Balasubramanian et al.
Exhibit 1039, filed Sep. 27, 2013 in connection with IPR2013-00011: Videotaped Deposition Transcript of Dr. Xiachai Liu, Mar. 20, 2013.
Exhibit 1040, filed Sep. 27, 2013 in connection with IPR2013-00011: Excerpt from videotaped Deposition Transcript of George M. Weinstock, Ph.D., Jun. 8, 2013.
Exhibit 1041, filed Sep. 27, 2013 in connection with IPR2013-00011: Seela et al., "Oligonucleotide Duplex Stability Controlled by the 7-Substituents of 7-Deazaguanine Bases," Bioorganic & Medical Chemistry Letters, vol. 5, No. 24, pp. 3049-3052, 1995.
Exhibit 1042, filed Sep. 27, 2013 in connection with IPR2013-00011: Ramzaeva et al., "123. 7-Deazaguanine DNA: Oligonucleotides with Hydrophobic or Cationic Side Chains," Helvetica Chimica Acta, vol. 80, pp. 1809-1822, 1997.
Exhibit 1043, filed Sep. 27, 2013 in connection with IPR2013-00011: Ramzaeva et al., "88. 7-Substituted 7-Deaza-2'-deoxyguanosines: Regioselective Halogenation of Pyrrolo[2,3-d]pyrimidine Nucleosides," Helvetica Chimica Acta, vol. 78, pp. 1083-1090, 1995.
Exhibit 1044, filed Sep. 27, 2013 in connection with IPR2013-00011: Seela et al., "Duplex Stability of Oligonucleotides Containing 7-Substituted 7-Deaza-and 8-Aza-7-Deazapurine Nucleosides," Nucleosides & Nucleotides, 16(7-9), pp. 963-966, 1997.
Exhibit 1045, filed Sep. 27, 2013 in connection with IPR2013-00011: Burgess et al., "Sytheses of Nucleosides Designed for Combinatorial DNA Sequencing," Chemistry—A European Journal, vol. 5, No. 3, pp. 951-960, 1999.
Exhibit 1046, filed Sep. 27, 2013 in connection with IPR2013-00011: U.S. Pat. No. 5,151,507, issued Sep. 29, 1992 to Hobbs, Jr. et al.
Exhibit 1047, filed Sep. 27, 2013 in connection with IPR2013-00011: U.S. Pat. No. 7,078,499, issued Jul. 18, 2006 to Odedra et al.
Exhibit 1048, filed Sep. 27, 2013 in connection with IPR2013-00011: GB Application No. 2000 0013276, filed. Jun. 1, 2000 by Odedra et al.
Exhibit 1049, filed Sep. 27, 2013 in connection with IPR2013-00011: Jan. 28, 2013 Declaration of Dr. Bruce P. Branchaud in Support of Petition for Inter Partes Review of U.S. Pat. No. 7,057,026.
Exhibit 1050, filed Sep. 27, 2013 in connection with IPR2013-00011: Lee et al., "DNA sequencing with dye-labeled terminators and T7 DNA polymerase: effect of dyes and dNTPs on incorporation of dye-terminators and probability analysis of termination fragments," Nucleic Acids Research, vol. 20, No. 10, pp. 2471-2433, 1992.
Exhibit 1051, filed Sep. 27, 2013 in connection with IPR2013-00011: http://www.answers.com/topic/incubate, Accessed Sep. 27, 2013.
Exhibit 1052, filed Sep. 27, 2013 in connection with IPR2013-00011: http://en.wikipedia.org/wiki/Fluorenylmethyloxycarbonyl_chloride, Accessed Sep. 27, 2013.
Exhibit 1053, filed Sep. 27, 2013 in connection with IPR2013-00011: Sep. 27, 2013 Declaration of Kevin Burgess.
Exhibit 1054, filed Sep. 27, 2013 in connection with IPR2013-00011: Fuji, et al., "An Improved Method for Methoxymethylation of Alcohols under Mild Acidic Conditions," Synthesis—The Journal of Synthetic Organic Chemistry, pp. 276-277, Apr. 1975.
Exhibit 2001, filed Jan. 7, 2013 in connection with IPR2013-00011: Composition of a Nucleotide.
Exhibit 2006, filed Apr. 26, 2013 in connection with IPR2013-00011: Dower patent with highlights.
Exhibit 2010, filed Jun. 24, 2013 in connection with IPR2013-00011: U.S. Pat. No. 8,088,575 (filed Jul. 19, 2010, issued Jan. 3, 2012) (Exhibit 1001 in IPR2013-00011).
Exhibit 2011, filed Jun. 24, 2013 in connection with IPR2013-00011: U.S. Pat. No. 7,713,698 (filed Aug. 20, 2007, issued May 11, 2010) (Exhibit 1001 in IPR2012-00006).
Exhibit 2012, filed Jun. 24, 2013 in connection with IPR2013-00011: U.S. Pat. No. 7,790,869 (filed Jun. 5, 2007, issued Sep. 7, 2010) (Exhibit 1001 in IPR2012-00007).
Exhibit 2013, filed Jun. 24, 2013 in connection with IPR2013-00011: Oct. 2, 2012 Declaration of George Weinstock Under 37 CFR 1.132 (Exhibit 1021 in IPR2013-00011).
Exhibit 2014, filed Jun. 24, 2013 in connection with IPR2013-00011: Petition for Inter Partes Review of U.S. Pat. No. 8,038,575 (Paper 4 in IPR2013-00011).
Exhibit 2015, filed Jun. 24, 2013 in connection with IPR2013-00011: Metzker et al. (1994) Termination of DNA synthesis by novel 3'-modified-deoxyribonucleoside 5'-triphosphates. Nucleic Acids Res. 22:4259-4267.
Exhibit 2016, filed Jun. 24, 2013 in connection with IPR2013-00011: Wu et al. (2007) Termination of DNA synthesis by N6-alkylated, not 3'-O-alkylated, photocleavable 2'-deoxyadenosine triphosphates. Nucleic Acids Res. 35:6339-6349.
Exhibit 2017, filed Jun. 24, 2013 in connection with IPR2013-00011: Sep. 15, 2012 Declaration of George Weinstock Under 37 CFR 1.132 (Exhibit 1021 in IPR2012-00007).
Exhibit 2018, filed Jun. 24, 2013 in connection with IPR2013-00011: Sep. 15, 2012 Declaration of George Weinstock Under 37 CFR 1.132 (Exhibit 1021 in IPR2012-00006).
Exhibit 2019, filed Jun. 24, 2013 in connection with IPR2013-00011: Definition of "DNA microarray." http://en/wikipedia.org/wiki/DNA_microarray.
Exhibit 2020, filed Jun. 24, 2013 in connection with IPR2013-00011: Brettin et al. (2005) Expression capable library for studies of *Neisseria gonorrhoeae*, version 1.0 BMC Microbiology. 5:50.
Exhibit 2021, filed Jun. 24, 2013 in connection with IPR2013-00011: George M. Weinstock, Handbook of Molecular Microbial Ecology, vol. 1—Chapter 18: The Impact of Next-Generation Sequencing Technologies on Metagenomics 141-147 Frans J. deBruijn ed., John Wiley & Sons, Inc. (2011).
Exhibit 2022, filed Jun. 24, 2013 in connection with IPR2013-00011: Sep. 16, 2012 Petition for Inter Partes Review of U.S. Pat. No. 7,713,698 (Paper 3 in IPR2012-00006).
Exhibit 2023, filed Jun. 24, 2013 in connection with IPR2013-00011: Sep. 16, 2012 Petition for Inter Partes Review of U.S. Pat. No. 7,790,869 (Paper 5 in IPR2012-00007).
Exhibit 2024, filed Jun. 24, 2013 in connection with IPR2013-00011: Maxam and Gilbert (1977) A new method for sequencing DNA, Proc. Natl. Acad. Sci. USA. 74:560-564.
Exhibit 2025, filed Jun. 24, 2013 in connection with IPR2013-00011: Sanger et al. (1977) DNA sequencing with chain -terminating inhibitors, Proc. Natl. Acad. Sci. USA. 74:5463-5467.
Exhibit 2026, filed Jun. 24, 2013 in connection with IPR2013-00011: Pennisi (2000) DOE Team Sequences Three Chromosomes, Science. 288:417-419.
Exhibit 2027, filed Jun. 24, 2013 in connection with IPR2013-00011: Welch and Burgess (1999) Synthesis of Fluorescent, Photolabile 3'-O-Protected nucleoside Triphosphates for the Base Addition Sequencing Scheme, nucleosides & Nucleotides. 18:197-201.
Exhibit 2028, filed Jun. 24, 2013 in connection with IPR2013-00011: Hyman (1998) A New Method of Sequencing DNA, Analytical Biochemistry 174:423-436.
Exhibit 2029, filed Jun. 24, 2013 in connection with IPR2013-00011: U.S. Pat. No. 5,302,509 (filed Feb. 27, 1991, issued Apr. 12, 1994).

(56) References Cited

OTHER PUBLICATIONS

Exhibit 2030, filed Jun. 24, 2013 in connection with IPR2013-00011: Canard and Sarfati (1994) DNA polymerase fluorescent substrates with reversible 3'-tags, Gene. 1481-6.
Exhibit 2031, filed Jun. 24, 2013 in connection with IPR2013-00011: U.S. Pat. No. 8,399,188 (filed Sep. 4, 2007, issued Mar. 19, 2013)
Exhibit 2032, filed Jun. 24, 2013 in connection with IPR2013-00011: Sarfati et al. (1987) Synthesis of Fluorescent or Biotinylated Nucleoside Compounds, Tetrahedron Letters. 43:3491-3497.
Exhibit 2033, filed Aug. 30, 2013 in connection with IPR2013-00011: Jun. 25, 2013 Substitute Declaration of Dr. George L. Trainor [redacted].
Exhibit 2034, filed Jun. 25, 2013 in connection with IPR2013-00011: Jingyue Ju et. al. (2006) Four-color DNA sequencing by synthesis using cleavable fluorescent nucleotide reversible terminators, Proceedings of the National Academy of Sciences. 103: 19635-19640.
Exhibit 2035, filed Jun. 25, 2012 in connection with IPR2013-00011: Batista et al. (2008) PRG-1 and 21U-RNAs Interact to Form the piRNA Complex Required for Fertility in C. elegans. Molecular Cell 31:1-12.
Exhibit 2036, filed Jun. 25, 2013 in connection with IPR2013-00011: Form 7 Review Context and Analysis, Biomedical Engineering and Research to Aid Persons with Disabilities Programs Dec. 19-20, 2000 Panel Review, Fluorescence Imaging Chip System for Massive Parallel DNA Sequencing. Proposal No. BES-0097793.
Exhibit 2037, filed Jun. 25, 2013 in connection with IPR2013-00011: Oct. 1, 2006 Request for opinion on manuscript by J. Ju et. al., Proceedings of National Academy of Sciences, U.S.A.
Exhibit 2038, filed Jun. 25, 2013 in connection with IPR2013-00011: Correspondence between George Rupp, Chancellor, Columbia University and Richard T. Schlossberg, President, The David and Lucile Packard Foundation (2001).
Exhibit 2039, filed Jun. 25, 2013 in connection with IPR2013-00011: The David and Lucile Packard Foundation, Packard Fellowships for Science and Engineering, http://www.packard.org/what-wefund/conservation-and-science/packard-fellowships-for-science-andengineering/ (last visited Jun. 25, 2013).
Exhibit 2040, filed Jun. 26, 2013 in connection with IPR2013-00011: "Chemistry for Next-Generation Sequencing." http://www.illumina.com/technology/sequencing_technology.ilmn.
Exhibit 2041, filed Jun. 26, 2013 in connection with IPR2013-00011: Chiang et al. (2010) Mammalian microRNA: experimental evaluation of novel and previously annotated genes, Genes & Dev. 24:992, 993.
Exhibit 2042, filed Jun. 26, 2013 in connection with IPR2013-00011: Seo et al. (2004) Photocleavable fluorescent nucleotides for DNA sequencing on a chip constructed by site-specific coupling chemistry, Proc. Natl Acad. Sci. 101(15):5483-5493.
Exhibit 2043, filed Jun. 26, 2013 in connection with IPR2013-00011: Curriculum vitae of Mr. Raymond S. Sims.
Exhibit 2044, filed Jun. 26, 2013 in connection with IPR2013-00011: Prior Testimony of Mr. Raymond S. Sims.
Exhibit 2045, filed Jun. 26, 2013 in connection with IPR2013-00011: Documents reviewed by Mr. Raymond S. Sims in this Proceeding.
Exhibit 2052, filed Jun. 26, 2013 in connection with IPR2013-00011: Gary Schroth Proof of Chiang Paper.
Exhibit 2074, filed Jun. 26, 2013 in connection with IPR2013-00011: Information about Dr. Ju's intellectual property sent to Illumina.
Exhibit 2090, filed Jun. 26, 2013 in connection with IPR2013-00011: IPR Default Protective Order.
Exhibit 2091, filed Jun. 26, 2013 in connection with IPR2013-00011: Declaration of Raymond S. Sims.
Exhibit 2092, filed Oct. 1, 2013 in connection with IPR2013-00011: Rough transcript of the Sep. 4, 2013 deposition of Dr. George L. Trainor.
Exhibit 2093, filed Oct. 1, 2013 in connection with IPR2013-00011: Excerpt from Protective Groups in Organic Synthesis, 3rd Ed. (Theodora W. Greene and Peter G.M. Wuts ed., John Wiley & Sons, Inc. 1999).
Exhibit 2094, filed Oct. 1, 2013 in connection with IPR2013-00011: Final transcript of the Sep. 4-6, 2013 deposition of Dr. George L. Trainor.
Exhibit 2095, filed Oct. 1, 2013 in connection with IPR2013-00011: Final transcript of the Sep. 3, 2013 deposition of Raymond S. Sims.
Nov. 18, 2013 Substitute Patent Owner Reply on Motion to Amend in connection with IPR2012-00006.
Nov. 12, 2013 Petitioner Motion to Exclude Evidence in connection with IPR2012-00006.
Exhibit 1056, filed Nov. 19, 2013 in connection with IPR2012-00006, IPR2012-00007, and IPR2013-00011: Videotaped Deposition Transcript of Kevin Burgess, Ph.D., Oct. 28, 2013, signed with errata.
Nov. 12, 2013 Patent Owner Motion for Observations on the Cross-Examination Testimony of Kevin Burgess, Ph.D. in connection with IPR2012-00006.
Nov. 12, 2013 Patent Owner Motion to Exclude Evidence in connection with IPR2012-00006.
Exhibit 2099, filed Nov. 12, 2013 in connection with IPR2012-00006, IPR2012-00007, and IPR2013-00011: Welch, M., et al (2005) Corrigenda to Syntheses of Nucleosides Designed for Combinatorial DNA Sequencing Chem. Eur.J., 1999, 951-960. Published in Chem. Eur. J, 2005, 11, 7136-7145.
Exhibit 2100, filed Nov. 12, 2013 in connection with IPR2012-00006, IPR2012-00007, and IPR2013-00011: Welch, M (1999) "Base Additions Sequencing Scheme (BASS) and Studies Toward New Sequencing Methodologies." PhD. Dissertation, Texas A&M University.
Exhibit 2101, filed Nov. 12, 2013 in connection with IPR2012-00006, IPR2012-00007, and IPR2013-00011: Lu and Burgess (2006) "A Diversity Oriented Synthesis of 3'-O-modified nucleoside triphosphates for DNA 'Sequencing by Synthesis'." Bioorganic & Medicinal Chemistry Letters, 16, 3902-3905.
Exhibit 2102, filed Nov. 12, 2013 in connection with IPR2012-00006, IPR2012-00007, and IPR2013-00011: Advanced Sequencing Technology Awards 2004. http://www.genome.gov/12513162 (accessed Oct. 14, 2013).
Exhibit 2103, filed Nov. 12, 2013 in connection with IPR2012-00006, IPR2012-00007, and IPR2013-00011: Welch and Burgess (2006) Erratum to Synthesis of Fluorescent, Photolabile 3'-O-Protected Nucleoside Triphosphates for the Base Addition Sequencing Scheme, Nucleosides & Nucleotides,18:197-201. Published in Nucleosides, Nucleotides and Nucleic Acids, 25:1, 119.
Nov. 26, 2013 Petitioner Response to Motion for Observations in connection with IPR2012-00006.
Nov. 26, 2013 Patent Owner Opposition to Petitioner's Motion to Exclude in connection with IPR2012-00006.
Nov. 26, 2013 Petitioner Opposition to Patentee's Motion to Exclude in connection with IPR2012-00006.
Dec. 3, 2013 Petitioner Reply to Patentee's Opposition to Motion to Exclude in connection with IPR2012-00006.
Dec. 3, 2013 Patent Owner Reply on Motion to Exclude in connection with IPR2012-00006.
Nov. 18, 2013 Substitute Patent Owner Reply on Motion to Amend in connection with IPR2012-00007.
Nov. 12, 2013 Petitioner Motion to Exclude Evidence in connection with IPR2012-00007.
Nov. 12, 2013 Patent Owner Motion for Observations on the Cross-Examination Testimony of Kevin Burgess, Ph.D. in connection with IPR2012-00007.
Nov. 12, 2013 Patent Owner Motion to Exclude Evidence in connection with IPR2012-00007.
Nov. 26, 2013 Petitioner Response to Motion for Observations in connection with IPR2012-00007.
Nov. 26, 2013 Patent Owner Opposition to Petitioner's Motion to Exclude in connection with IPR2012-00007.
Nov. 26, 2013 Petitioner Opposition to Patentee's Motion to Exclude in connection with IPR2012-00007.
Dec. 3, 2013 Petitioner Reply to Patentee's Opposition to Motion to Exclude in connection with IPR2012-00007.
Dec. 3, 2013 Patent Owner Reply on Motion to Exclude in connection with IPR2012-00007.

(56) References Cited

OTHER PUBLICATIONS

Nov. 18, 2013 Substitute Patent Owner Reply on Motion to Amend in connection with IPR2013-00011.
Nov. 12, 2013 Petitioner Motion to Exclude Evidence in connection with IPR2013-00011.
Nov. 12, 2013 Patent Owner Motion for Observations on the Cross-Examination Testimony of Kevin Burgess, Ph.D. in connection with IPR2013-00011.
Nov. 12, 2013 Patent Owner Motion to Exclude Evidence in connection with IPR2013-00011.
Nov. 26, 2013 Petitioner Response to Motion for Observations in connection with IPR2013-00011.
Nov. 26, 2013 Patent Owner Opposition to Petitioner's Motion to Exclude in connection with IPR2013-00011.
Nov. 26, 2013 Petitioner Opposition to Patentee's Motion to Exclude in connection with IPR2013-00011.
Dec. 3, 2013 Petitioner Reply to Patentee's Opposition to Motion to Exclude in connection with IPR2013-00011.
Dec. 3, 2013 Patent Owner Reply on Motion to Exclude in connection with IPR2013-00011.
Sep. 16, 2012 Petition for Inter Partes Review of U.S. Pat. No. 7,713,698, issued May 11, 2010.
Sep. 16, 2012 Motion to Waive Page Limit and Proposed Petition in connection with Petition for Inter Partes Review of U.S. Pat. No. 7,713,698, issued May 11, 2010.
Dec. 20, 2012 Preliminary Response under 37 C.F.R. 42.107 in connection with IPR2012-00006.
Mar. 12, 2013 Decision on Petition for Inter Partes Review in connection with IPR2012-00006.
Mar. 26, 2013 Request for Reconsideration in connection with IPR2012-00006.
Apr. 26, 2013 Opposition to Request for Reconsideration (Rehearing) Under 37 C.F.R. 42.71.(C) in connection with IPR2012-00006.
May 10, 2013 Decision on Request for Rehearing in connection with IPR2012-00006.
Aug. 30, 2013 Substitute Patent Owner Response Under 37 C.F.R. 42.120 in connection with IPR2012-00006.
Aug. 30, 2013 Substitute Patent Owner Motion to Amend Under 37 C.F.R. 42.121 in connection with IPR2012-00006.
Sep. 27, 2013 Petitioner Opposition to Motion to Amend in connection with IPR2012-00006.
Sep. 27, 2013 Petitioner Reply to Response to Petition in connection with IPR2012-00006.
Oct. 28, 2013 Patent Owner Reply on Motion to Amend in connection with IPR2012-00006.
Exhibit 1001, filed Sep. 16, 2012 in connection with IPR2012-00006: U.S. Pat. No. 7,713,698, issued May 11, 2010 to Ju et al.
Exhibit 1002, filed Sep. 16, 2012 in connection with IPR2012-00006: PCT International Application No. PCT/US90/06678 filed Oct. 26, 1990, published on May 16, 1991 as Publication No. WO 91/06678 to SRI International.
Exhibit 1003, filed Sep. 16, 2012 in connection with IPR2012-00006: Prober et al. (1987), "A System for Rapid DNA Sequencing with Fluorescent Chain-Terminating Dideoxynucleotides", *Science* vol. 238, Oct. 16, 1987, pp. 336-341.
Exhibit 1004, filed Sep. 16, 2012 in connection with IPR2012-00006: U.S. Pat. No. 5,242,796 issued Sep. 7, 1993 to Prober et al.
Exhibit 1005, filed Sep. 16, 2012 in connection with IPR2012-00006: U.S. Pat. No. 5,547,839 issued Aug. 20, 1996 to Dower et al.
Exhibit 1006, filed Sep. 16, 2012 in connection with IPR2012-00006: PCT International Application No. PCT/US96/02342 filed Feb. 21, 1996, published on Sep. 6, 1996 as Publication No. WO 96/27025 to Ely Rabani.
Exhibit 1007, filed Sep. 16, 2012 in connection with IPR2012-00006: PCT International Application No. PCT/GB00/00873 filed Mar. 10, 2000, published on Sep. 14, 2000 as Publication No. WO 00/53805 to ASM Scientific, Inc.
Exhibit 1008, filed Sep. 16, 2012 in connection with IPR2012-00006: U.S. Pat. No. 7,270,951 issued Sep. 18, 2007 to Stemple et al.

Exhibit 1009, filed Sep. 16, 2012 in connection with IPR2012-00006: U.S. Application for A Method for Direct Nucleic Acid Sequencing; U.S. Appl. No. 09/266,187 filed Mar. 10, 1999.
Exhibits 1010-1012, filed Sep. 16, 2012 in connection with IPR2012-00006: PCT International Application No. PCT/JP97/00239, filed Jan. 31, 1997, published on Aug. 6, 1998 as Publication No. WO 98/33939 to Hitachi, Ltd. with certified English translation, and Translation Affidavit.
Exhibit 1013, filed Sep. 16, 2012 in connection with IPR2012-00006: U.S. Pat. No. 5,047,519 issued Sep. 10, 1991 to Hobbs, Jr. et al.
Exhibit 1014, filed Sep. 16, 2012 in connection with IPR2012-00006: U.S. Pat. No. 4,804,748 issued Feb. 14, 1989 to Seela.
Exhibit 1015, filed Sep. 16, 2012 in connection with IPR2012-00006: U.S. Pat. No. 5,844,106 issued Dec. 1, 1998 to Seela et al.
Exhibit 1016, filed Sep. 16, 2012 in connection with IPR2012-00006: PCT International Application No. PCT/US89/02170, filed May 18, 1989, published on Nov. 30, 1989 as Publication No. WO 89/11548 to Cetus Corporation.
Exhibit 1017, filed Sep. 16, 2012 in connection with IPR2012-00006: U.S. Pat. No. 7,037,687 issued May 2, 2006 to Williams et al.
Exhibit 1018, filed Sep. 16, 2012 in connection with IPR2012-00006: U.S. Pat. No. 6,255,083 issued Jul. 3, 2001 to Williams.
Exhibit 1019, filed Sep. 16, 2012 in connection with IPR2012-00006: U.S. Pat. No. 6,001,566 issued Dec. 14, 1999 to Canard et al.
Exhibit 1020, filed Sep. 16, 2012 in connection with IPR2012-00006: PCT International Application No. PCT/GB93/00848, filed Apr. 22, 1993, published on Oct. 28, 1993 as Publication No. WO 93/21340 to Medical Research Council.
Exhibit 1021, filed Sep. 16, 2012 in connection with IPR2012-00006: Sep. 15, 2012 Declaration of George Weinstock Under Rule 37 C.F.R. §1.132.
Exhibit 1022, filed Sep. 16, 2012 in connection with IPR2012-00006: Excerpts of File History of U.S. Pat. No. 7,713,698.
Exhibit 1025, filed Apr. 30, 2013 in connection with IPR2012-00006: Columbia's Amended Complaint from The Trustees of Columbia University in the *City of New York v. Illumina, Inc.*, D. Del C.A. No. 12-376 (GMS), filed Apr. 11, 2012.
Exhibit 1026, filed Apr. 30, 2013 in connection with IPR2012-00006: Illumina's Answer to Amended Complaint from The Trustees of Columbia University in the *City of New York v. Illumina, Inc.*, D. Del C.A. No. 12-376 (GMS), filed Dec. 21, 2012.
Exhibit 1029, filed Jun. 18, 2013 in connection with IPR2012-00006: U.S. Pat. No. 4,772,691, issued Sep. 20, 1988 to Herman.
Exhibit 1030, filed Jun. 18, 2013 in connection with IPR2012-00006: Rosenblum et al., "New Dye-Labeled Terminators for Improved DNA Sequencing Patterns," Nucleic Acid Research, 1997, vol. 25, No. 22, pp. 4500-4504.
Exhibit 1031, filed Jun. 18, 2013 in connection with IPR2012-00006: PCT International Publication No. WO 99/49082, published Sep. 30, 1999 to Invitrogen Corporation.
Exhibit 1032, filed Jun. 18, 2013 in connection with IPR2012-00006: U.S. Pat. No. 5,449,767, issued Sep. 12, 1995 to Ward et al.
Exhibit 1033, filed Jun. 18, 2013 in connection with IPR2012-00006: U.S. Pat. No. 5,948,648, issued Sep. 7, 1999 to Khan et al.
Exhibit 1034, filed Jun. 18, 2013 in connection with IPR2012-00006: Jun. 8, 2013 Videotaped Deposition Transcript of George M. Weinstock, Ph.D.
Exhibit 1036, filed Sep. 27, 2013 in connection with IPR2012-00006: "Next Generation Genomics: World Map of High-throughput Sequencers," Sep. 1, 2013.
Exhibit 1037, filed Sep. 27, 2013 in connection with IPR2012-00006: GB Application No. 2001 0029012, filed Dec. 4, 2001 by Balasubramanian et al.
Exhibit 1039, filed Sep. 27, 2013 in connection with IPR2012-00006: Videotaped Deposition Transcript of Dr. Xiaohai Liu, Mar. 20, 2013.
Exhibit 1040, filed Sep. 27, 2013 in connection with IPR2012-00006: Excerpt from videotaped Deposition Transcript of George M. Weinstock, Ph.D., Jun. 8, 2013.
Exhibit 1041, filed Sep. 27, 2013 in connection with IPR2012-00006: Seela et al., "Oligonucleotide Duplex Stability Controlled by the 7-Substituents of 7-Deazaguanine Bases," Bioorganic & Medical Chemistry Letters, vol. 5, No. 24, pp. 3049-3052, 1995.

(56) References Cited

OTHER PUBLICATIONS

Exhibit 1042, filed Sep. 27, 2013 in connection with IPR2012-00006: Ramzaeva et al., "123. 7-Deazaguanine DNA: Oligonucleotides with Hydrophobic or Cationic Side Chains," Helvetica Chimica Acta, vol. 80, pp. 1809-1822, 1997.
Exhibit 1043, filed Sep. 27, 2013 in connection with IPR2012-00006: Ramzaeva et al., "88. 7-Substituted 7-Deaza-2'-deoxyguanosines: Regioselective Halogenation of Pyrrolo[2,3-d]pyrimidine Nucleosides," Helvetica Chimica Acta, vol. 78, pp. 1083-1090, 1995.
Exhibit 1044, filed Sep. 27, 2013 in connection with IPR2012-00006: Seela et al., "Duplex Stability of Oligonucleotides Containing 7-Substituted 7-Deaza-and 8-Aza-7-Deazapurine Nucleosides," Nucleosides & Nucleotides, 16(7-9), pp. 963-966, 1997.
Exhibit 1045, filed Sep. 27, 2013 in connection with IPR2012-00006: Burgess et al., "Syntheses of Nucleosides Designed for Combinatorial DNA Sequencing," Chemistry—A European Journal, vol. 5, No. 3, pp. 951-960, 1999.
Exhibit 1046, filed Sep. 27, 2013 in connection with IPR2012-00006: U.S. Pat. No. 5,151,507, issued Sep. 29, 1992 to Hobbs, Jr. et al.
Exhibit 1047, filed Sep. 27, 2013 in connection with IPR2012-00006: U.S. Pat. No. 7,078,499, issued Jul. 18, 2006 to Odedra et al.
Exhibit 1048, filed Sep. 27, 2013 in connection with IPR2012-00006: GB Application No. 2000 0013276, filed Jun. 1, 2000 by Odedra et al.
Exhibit 1049, filed Sep. 27, 2013 in connection with IPR2012-00006: Jan. 28, 2013 Declaration of Dr. Bruce P. Branchaud in Support of Petition for Inter Partes Review of U.S. Pat. No. 7,057,026.
Exhibit 1050, filed Sep. 27, 2013 in connection with IPR2012-00006: Lee et al., "DNA sequencing with dye-labeled terminators and T7 DNA polymerase: effect of dyes and dNTPs on incorporation of dye-terminators and probability analysis of termination fragments," Nucleic Acids Research, vol. 20, No. 10, pp. 2471-2483, 1992.
Exhibit 1051, filed Sep. 27, 2013 in connection with IPR2012-00006: http://www.answers.com/topic/incubate, Accessed Sep. 27, 2013.
Exhibit 1052, filed Sep. 27, 2013 in connection with IPR2012-00006: http://en.wikipedia.org/wiki/Fluorenylmethyloxycarbonyl_chloride, Accessed Sep. 27, 2013.
Exhibit 1053, filed Sep. 27, 2013 in connection with IPR2012-00006: Sep. 27, 2013 Declaration of Kevin Burgess.
Exhibit 1054, filed Sep. 27, 2013 in connection with IPR2012-00006: Fuji, et al., "An Improved Method for Methoxymethylation of Alcohols under Mild Acidic Conditions," Synthesis—The Journal of Synthetic Organic Chemistry, pp. 276-277, Apr. 1975.
Exhibit 2001, filed Dec. 20, 2012 in connection with IPR2012-00006: U.S. Pat. No. 5,383,858, issued Jan. 24, 1995 to Reilly et al.
Exhibit 2006, filed Apr. 26, 2013 in connection with IPR2012-00006: Dower patent with highlights.
Exhibit 2010, filed Jun. 24, 2013 in connection with IPR2012-00006: U.S. Pat. No. 8,088,575 (filed Jul. 19, 2010, issued Jan. 3, 2012) (Exhibit 1001 in IPR2013-00011).
Exhibit 2011, filed Jun. 24, 2013 in connection with IPR2012-00006: U.S. Pat. No. 7,713,698 (filed Aug. 20, 2007, issued May 11, 2010) (Exhibit 1001 in IPR2012-00006).
Exhibit 2012, filed Jun. 24, 2013 in connection with IPR2012-00006: U.S. Pat. No. 7,790,869 (filed Jun. 5, 2007, issued Sep. 7, 2010) (Exhibit 1001 in IPR2012-00007).
Exhibit 2013, filed Jun. 24, 2013 in connection with IPR2012-00006: Oct. 2, 2012 Declaration of George Weinstock Under 37 CFR 1.132 (Exhibit 1021 in IPR2013-00011).
Exhibit 2014, filed Jun. 24, 2013 in connection with IPR2012-00006: Petition for Inter Partes Review of U.S. Pat. No. 8,088,575 (Paper 4 in IPR2013-00011).
Exhibit 2015, filed Jun. 24, 2013 in connection with IPR2012-00006: Metzker et al. (1994) Termination of DNA synthesis by novel 3'-modified-deoxyribonucleoside 5'-triphosphates. Nucleic Acids Res. 22:4259-4267.
Exhibit 2016, filed Jun. 24, 2013 in connection with IPR2012-00006: Wu et al. (2007) Termination of DNA synthesis by N6-alkylated, not 3'-O-alkylated, photocleavable 2'-deoxyadenosine triphosphates. Nucleic Acids Res. 35:6339-6349.
Exhibit 2017, filed Jun. 24, 2013 in connection with IPR2012-00006: Sep. 15, 2012 Declaration of George Weinstock Under 37 CFR 1.132 (Exhibit 1021 in IPR2012-00007).
Exhibit 2018, filed Jun. 24, 2013 in connection with IPR2012-00006: Sep. 15, 2012 Declaration of George Weinstock Under 37 CFR 1.132 (Exhibit 1021 in IPR2012-00006).
Exhibit 2019, filed Jun. 24, 2013 in connection with IPR2012-00006: Definition of "DNA microarray."http://en/wikipedia.org/wiki/DNA microarray.
Exhibit 2020, filed Jun. 24, 2013 in connection with IPR2012-00006: Brettin et al. (2005) Expression capable library for studies of Neisseria gonorrhoeae, version 1.0 BMC Microbiology. 5:50.
Exhibit 2021, filed Jun. 24, 2013 in connection with IPR2012-00006: George M. Weinstock, Handbook of Molecular Microbial Ecology, vol. 1—Chapter 18: The Impact of Next-Generation Sequencing Technologies on Metagenomics 141-147 Frans J. deBruijn ed., John Wiley & Sons, Inc. (2011).
Exhibit 2022, filed Jun. 24, 2013 in connection with IPR2012-00006: Sep. 16, 2012 Petition for Inter Partes Review of U.S. Pat. No. 7,713,698 (Paper 3 in IPR2012-00006).
Exhibit 2023, filed Jun. 24, 2013 in connection with IPR2012-00006: Sep. 16, 2012 Petition for Inter Partes Review of U.S. Pat. No. 7,790,869 (Paper 5 in IPR2012-00007).
Exhibit 2024, filed Jun. 24, 2013 in connection with IPR2012-00006: Maxam and Gilbert (1977) A new method for sequencing DNA, Proc. Natl. Acad. Sci. USA. 74:560-564.
Exhibit 2025, filed Jun. 24, 2013 in connection with IPR2012-00006: Sanger et al. (1977) DNA sequencing with chain-terminating inhibitors, Proc. Natl. Acad. Sci. USA. 74:5463-5467.
Exhibit 2026, filed Jun. 24, 2013 in connection with IPR2012-00006: Pennisi (2000) DOE Team Sequences Three Chromosomes, Science. 288:417-419.
Exhibit 2027, filed Jun. 24, 2013 in connection with IPR2012-00006: Welch and Burgess (1999) Synthesis of Fluorescent, Photolabile 3'-O-Protected nucleoside Triphosphates for the Base Addition Sequencing Scheme, nucleosides & Nucleotides. 18:197-201.
Exhibit 2028, filed Jun. 24, 2013 in connection with IPR2012-00006: Hyman (1998) A New Method of Sequencing DNA, Analytical Biochemistry 174:423-436.
Exhibit 2029, filed Jun. 24, 2013 in connection with IPR2012-00006: U.S. Pat. No. 5,302,509 (filed Feb. 27, 1991, issued Apr. 12, 1994).
Exhibit 2030, filed Jun. 24, 2013 in connection with IPR2012-00006: Canard and Sarfati (1994) DNA polymerase fluorescent substrates with reversible 3'-tags, Gene. 1481-6.
Exhibit 2031, filed Jun. 24, 2013 in connection with IPR2012-00006: U.S. Pat. No. 8,399,188 (filed Sep. 4, 2007, issued Mar. 19, 2013).
Exhibit 2032, filed Jun. 24, 2013 in connection with IPR2012-00006: Sarfati et al. (1987) Synthesis of Fluorescent or Biotinylated Nucleoside Compounds, Tetrahedron Letters. 43:3491-3497.
Exhibit 2033, filed Aug. 30, 2013 in connection with IPR2012-00006: Jun. 25, 2013 Substitute Declaration of Dr. George L. Trainor [redacted].
Exhibit 2034, filed Jun. 25, 2013 in connection with IPR2012-00006: Jingyue Ju et. al. (2006) Four-color DNA sequencing by synthesis using cleavable fluorescent nucleotide reversible terminators, Proceedings of the National Academy of Sciences. 103: 19635-19640.
Exhibit 2035, filed Jun. 25, 2013 in connection with IPR2012-00006: Batista et al. (2008) PRG-1 and 21U-RNAs Interact to Form the piRNA Complex Required for Fertility in C. elegans. Molecular Cell 31:1-12.
Exhibit 2036, filed Jun. 25, 2013 in connection with IPR2012-00006: Form 7 Review Context and Analysis, Biomedical Engineering and Research to Aid Persons with Disabilities Programs Dec. 19-20, 2000 Panel Review, Fluorescence Imaging Chip System for Massive Parallel DNA Sequencing. Proposal No. BES-0097793.
Exhibit 2037, filed Jun. 25, 2013 in connection with IPR2012-00006: Oct. 1, 2006 Request for opinion on manuscript by J. Ju et. al., Proceedings of National Academy of Sciences, U.S.A.
Exhibit 2038, filed Jun. 25, 2013 in connection with IPR2012-00006: Correspondence between George Rupp, Chancellor, Columbia University and Richard T. Schlossberg, President, The David and Lucile Packard Foundation (2001).

(56) References Cited

OTHER PUBLICATIONS

Exhibit 2039, filed Jun. 25, 2013 in connection with IPR2012-00006: The David and Lucile Packard Foundation, Packard Fellowships for Science and Engineering, http://www.packard.org/what-wefund/conservation-and-science/packard-fellowships-for-science-andengineering/ (last visited Jun. 25, 2013).

Exhibit 2040, filed Jun. 25, 2013 in connection with IPR2012-00006: "Chemistry for Next-Generation Sequencing." http://www.illumina.com/technology/sequencing_technology.ilmn.

Exhibit 2041, filed Jun. 25, 2013 in connection with IPR2012-00006: Chiang et al. (2010) Mammalian microRNAs: experimental evaluation of novel and previously annotated genes, Genes & Dev. 24:992, 993.

Exhibit 2042, filed Jun. 25, 2013 in connection with IPR2012-00006: Seo et al. (2004) Photocleavable fluorescent nucleotides for DNA sequencing on a chip constructed by site-specific coupling chemistry, Proc. Natl Acad. Sci. 101(15):5488-5493.

Exhibit 2043, filed Jun. 25, 2013 in connection with IPR2012-00006: Curriculum vitae of Mr. Raymond S. Sims.

Exhibit 2044, filed Jun. 25, 2013 in connection with IPR2012-00006: Prior Testimony of Mr. Raymond S. Sims.

Exhibit 2045, filed Jun. 25, 2013 in connection with IPR2012-00006: Documents reviewed by Mr. Raymond S. Sims in this Proceeding.

Exhibit 2052, filed Jun. 25, 2013 in connection with IPR2012-00006: Gary Schroth Proof of Chiang Paper.

Exhibit 2074, filed Jun. 25, 2013 in connection with IPR2012-00006: Information about Dr. Ju's intellectual property sent to Illumina.

Exhibit 2090, filed Jun. 26, 2013 in connection with IPR2012-00006: IPR Default Protective Order.

Exhibit 2091, filed Jun. 26, 2013 in connection with IPR2012-00006: Declaration of Raymond S. Sims.

Exhibit 2092, filed Oct. 10, 2013 in connection with IPR2012-00006: Rough Transcript of the Sep. 4, 2013 deposition of Dr. George L. Trainor.

Exhibit 2093, filed Oct. 1, 2013 in connection with IPR2012-00006: Excerpt from Protective Groups in Organic Synthesis, 3rd Ed. (Theodora W. Greene and Peter G.M. Wuts ed., John Wiley & Sons, Inc. 1999).

Exhibit 2094, filed Oct. 1, 2013 in connection with IPR2012-00006: Final transcript of the Sep. 4-6, 2013 deposition of Dr. George L. Trainor.

Exhibit 2095, filed Oct. 1, 2013 in connection with IPR2012-00006: Final transcript of the Sep. 3, 2013 deposition of Raymond S. Sims.

Exhibit 2105, filed Dec. 15, 2013 in connection with IPR2012-00006, IPR2012-00007, and IPR2013-00011: Columbia's Demonstratives Under 42.70(b) for Dec. 17, 2013 Oral Hearing.

Exhibit 1057, filed Dec. 16, 2013 in connection with IPR2012-00006, IPR2012-00007, and IPR2013-00011: Illumina's Invalidity Demonstratives for Final Hearing Dec. 17, 2013.

Pending claims in U.S. Appl. No. 13/186,353, filed Jul. 19, 2011 by Ju et al. (published as 2012/0156680 A1, Jun. 21, 2012).

Pending claims in U.S. Appl. No. 14/242,487, filed Apr. 1, 2014 by Ju et al. (published as 2014/0315191 A1, Oct. 23, 2014).

\* cited by examiner

A.

B.

A.

B.

(2) Pyrosequencing results after 1st extension with Allyl-dGTP (1) Pyrosequencing results with dNTPs (4) Pyrosequencing results after 3rd extension with Allyl-dGTP (3) Pyrosequencing results after 2nd extension with Allyl-dGTP Sequencing the sepharose beads immobilized with DNA with Normal Nucleotides

SEQUENCE LISTING

<160> NUMBER OF SEQ ID NOS: 10

<210> SEQ ID NO 1
<211> LENGTH: 18
<212> TYPE: DNA
<213> ORGANISM: Artificial Sequence
<220> FEATURE:
<223> OTHER INFORMATION: chemically synthesized

<400> SEQUENCE: 1
agaggatcca accgagac                                                 18

<210> SEQ ID NO 2
<211> LENGTH: 18
<212> TYPE: DNA
<213> ORGANISM: Artificial Sequence
<220> FEATURE:

<223> OTHER INFORMATION: chemically synthesized

<400> SEQUENCE: 2
cagagccaac ctaggaga                                                 18

<210> SEQ ID NO 3
<211> LENGTH: 58
<212> TYPE: DNA
<213> ORGANISM: Artificial Sequence
<220> FEATURE:
<223> OTHER INFORMATION: chemically synthesized

<400> SEQUENCE: 3
tttttatcga attcccggaa acagctatga ccatgcttgc atggtcatag ctgtttcc     58

<210> SEQ ID NO 4
<211> LENGTH: 5
<212> TYPE: DNA
<213> ORGANISM: Artificial Sequence
<220> FEATURE:
<223> OTHER INFORMATION: chemically synthesized

<400> SEQUENCE: 4 ttccc                                                                5

<210> SEQ ID NO 5
<211> LENGTH: 6
<212> TYPE: DNA
<213> ORGANISM: Artificial Sequence
<220> FEATURE:
<223> OTHER INFORMATION: chemically synthesized

<400> SEQUENCE: 5 ttcccg                                                               6

<210> SEQ ID NO 6
<211> LENGTH: 22
<212> TYPE: DNA
<213> ORGANISM: Artificial Sequence
<220> FEATURE:
<223> OTHER INFORMATION: chemically synthesized

<400> SEQUENCE: 6
gtatgcagtt agctgtctgg cc                                            22

<210> SEQ ID NO 7
<211> LENGTH: 40
<212> TYPE: DNA
<213> ORGANISM: Artificial Sequence
<220> FEATURE:
<223> OTHER INFORMATION: chemically synthesized

<400> SEQUENCE: 7
catacgtcaa tcgacagacc ggtttaaagg gccctactgc                         40

<210> SEQ ID NO 8
<211> LENGTH: 19
<212> TYPE: DNA
<213> ORGANISM: Artificial Sequence
<220> FEATURE:
<223> OTHER INFORMATION: chemically synthesized

<400> SEQUENCE: 8
agaggatcca accgagact                                                19

```
<210> SEQ ID NO 9
<211> LENGTH: 18
<212> TYPE: DNA
<213> ORGANISM: Artificial Sequence
<220> FEATURE:
<223> OTHER INFORMATION: primer directed to human p53 gene

<400> SEQUENCE: 9
agaggatcca accgagac                                                 18

<210> SEQ ID NO 10
<211> LENGTH: 60
<212> TYPE: DNA
<213> ORGANISM: homo sapiens

<400> SEQUENCE: 10
gtgtacatca acatcaccta ccaccatgtc agtctcggtt ggatcctcta ttgtgtccgg   60
```

PYROSEQUENCING METHODS AND RELATED COMPOSITIONS

This application is a §371 national stage of PCT International Application No. PCT/US2006/024157, filed Jun. 20, 2006, and claims the benefit of U.S. Provisional Application No. 60/692,816, filed Jun. 21, 2005, the contents of which are hereby incorporated by reference.

The invention disclosed herein was made with government support under a grant from the Center for Excellence in Genomic Science Grant No. P50 HG002806. Accordingly, the U.S. Government has certain rights in this invention.

Throughout this application, various publications are referenced in parentheses by number. Full citations for these references may be found at the end of the specification immediately preceding the claims. The disclosures of these publications in their entireties are hereby incorporated by reference into this application to more fully describe the state of the art to which this invention pertains.

BACKGROUND OF THE INVENTION

Pyrosequencing is a method based on the detection of the pyrophosphate group that is generated when a nucleotide is incorporated in a DNA polymerase reaction [1]. Each of the four deoxynucleotides (dNTPs) is added sequentially to the DNA template to be sequenced with a cocktail of enzymes and substrates in addition to the usual polymerase reaction components. If the added nucleotide is complementary with the first available base on the template, the nucleotide will be incorporated and a pyrophosphate will be released. The released pyrophosphate is converted to ATP by sulfurylase, and this ATP is the substrate for a luciferase, e.g. firefly luciferase, which reaction produces visible light. If the added nucleotide is not incorporated, no light will be produced and the nucleotide will simply be degraded by the enzyme apyrase. This pyrosequencing technique, schematized in FIG. 1, has been applied to single nucleotide polymorphism (SNP) detection and other applications [2].

There are, however, inherent difficulties in the traditional pyrosequencing method for determining the number of incorporated nucleotides in homopolymeric regions (e.g. a string of several T's in a row) of the template. Moreover, dATP greatly interferes with the luciferase detection system, which is deficient in the detection of dATP.

SUMMARY OF THE INVENTION

This invention provides a method for determining the nucleotide sequence of a single-stranded DNA comprising performing the following steps for each nucleic acid residue of the DNA whose identity is to be determined:

(a) contacting the DNA under DNA polymerization-permitting conditions with (i) a 3'-O-blocked dNTP selected from the group consisting of 3'-O-blocked dATP, 3'-O-blocked dCTP, 3'-D-blocked dGTP, and 3'-O-blocked dTTP, and (ii) 9°N DNA polymerase (exo−) A4851/Y409V or another DNA polymerase able to incorporate 3'-O-blocked dNTPs;

(b) (i) determining whether pyrophosphate is generated as a result of step (a), whereby (1) pyrophosphate generation indicates that polymerization has occurred and the identity of the nucleic acid residue in the DNA is that which is complementary to the 3'-O-blocked dNTP used in part (i) of step (a), and (2) the absence of pyrophosphate generation indicates that the identity of such nucleic acid residue is not that which is complementary to such 3'-O-blocked dNTP, and (ii) if pyrophosphate is not generated, repeating step (a) once, twice or three times as necessary, wherein in each repetition a 3'-O-blocked dNTP is used which is different from any 3'-O-blocked dNTP already used, and determining, after each repetition of step (a), whether pyrophosphate is generated, such generation indicating that polymerization has occurred and the identity of the nucleic acid residue in the DNA is that which is complementary to the 3'-O-blocked dNTP used in part (i) of the repeated step (a); and (c) removing from the 3'-O-blocked dNTP polymerized in step (a) or (b), whichever is applicable, the moiety blocking the 3'-O atom of the dNTP, with the proviso that such removing step is optional in the event that there remains no further nucleic acid residue of the DNA whose identity is to be determined.

DETAILED DESCRIPTION OF THE INVENTION

Definitions

Figure 1:
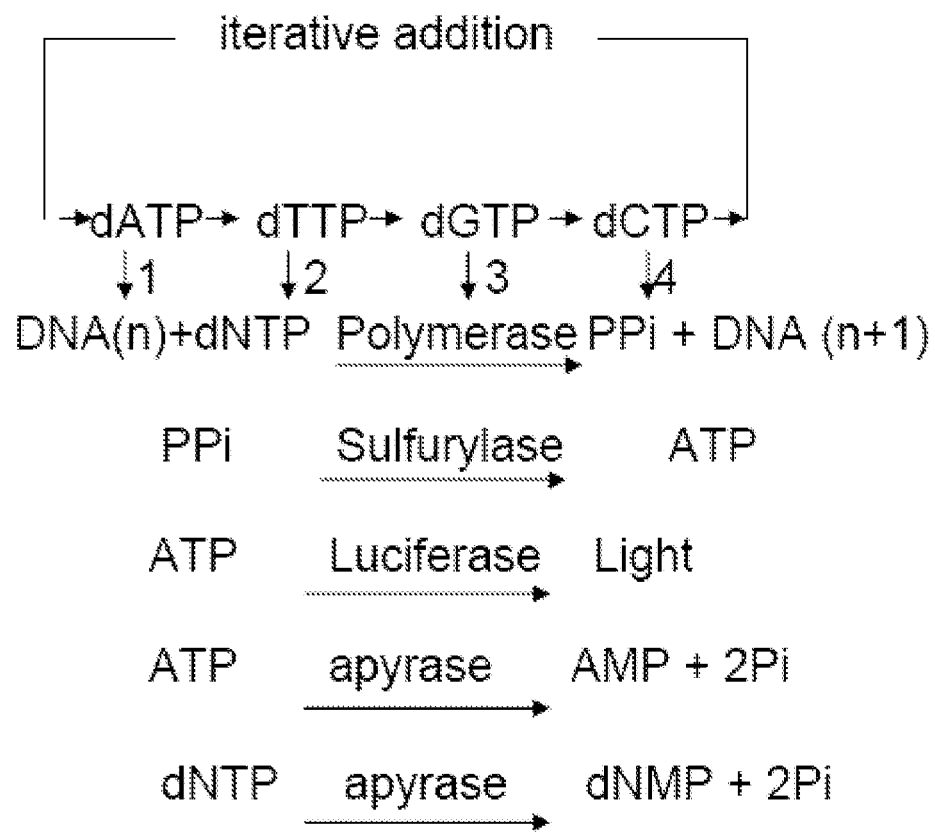
FIG. 1: Schematic of pyrosequencing in solution. Reactants not shown are APS, which with PPi is converted to ATP and $SO_4^{2-}$ by ATP-sulfurylase. In addition luciferase acts on ATP, luciferin and $O_2$ to give AMP, PPi, oxyluciferin, $CO_2$ and light, and apyrase converts ATP and dNTP to AMP, dNMP and 2 Pi.

As used herein, and unless stated otherwise, each of the following terms shall have the definition set forth below.
PPi—pyrophosphate
dNTP—deoxynucleoside 5'-triphosphate—also known as a deoxynucleotide
APS—adenosine 5'-phosphosulfate
ATP—adenosine 5'-triphosphate
dATP—deoxyadenosine 5'-triphosphate
THF—tetrahydrofuran
TEAB—tetraethylammonium bromide
TPPTS—tri sodium salt of tri (m-sulfophenyl)-phosphine
"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

Embodiments of the Invention

Disclosed here is a method that solves the problems of homopolymeric regions and dATP interference by using 3'-O-allyl-nucleotides as reversible terminators in pyrosequencing using either a new PPi detection system (Chemosensing Ensemble), or the traditional luciferase detection technique.

Specifically, this invention provides a method for determining the nucleotide sequence of a single-stranded DNA comprising performing the following steps for each nucleic acid residue of the DNA whose identity is to be determined:
(a) contacting the DNA under DNA polymerization-permitting conditions with (i) a 3'-O-blocked dNTP selected from the group consisting of 3'-O-blocked dATP, 3'-O-blocked dCTP, 3'-O-blocked dGTP, and 3'-O-blocked dTTP, and (ii) 9°N DNA polymerase (exo−) A485I/Y409V or other DNA polymerase;
(b) (i) determining whether pyrophosphate is generated as a result of step (a), whereby (1) pyrophosphate generation indicates that polymerization has occurred and the identity of the nucleic acid residue in the DNA is that which is complementary to the 3'-O-blocked dNTP used in part (i) of step (a), and (2) the absence of pyrophosphate generation indicates that the identity of such nucleic acid residue is not that which is complementary to such 3'-O-blocked dNTP, and (ii) if pyrophosphate is not generated, repeating step (a) once, twice or three times as necessary (i.e. until pyrophosphate is generated), wherein in each repetition a 3'-O-blocked dNTP is used which is different from any 3'-O-blocked dNTP already used, and determining, after each repetition of step (a), whether pyrophosphate is generated, such generation indicating that polymerization has occurred and the identity of the nucleic acid residue in the DNA is that which is complementary to the 3'-O-blocked dNTP used in part (i) of the repeated step (a); and
(c) removing from the 3'-O-blocked dNTP polymerized in step (a) or (b), whichever is applicable, the moiety blocking the 3'-O atom of the dNTP, with the proviso that such removing step is optional in the event that there remains no further nucleic acid residue of the DNA whose identity is to be determined.

The identity of a nucleic acid residue in the DNA being sequenced is that which is complementary to the 3'-O-blocked dNTP incorporated, i.e. such identity is determined by the well-established complementary base-pairing rules. For example, if a 3'-O-blocked dATP is incorporated, then the corresponding nucleic acid residue in the DNA being sequenced is a thymine. If a 3'-O-blocked dGTP is incorporated, then the corresponding nucleic acid residue in the DNA being sequenced is a cytosine, and so forth with the understanding that adenine and thymine are complements of each other, and guanine and cytosine are complements of each other. In addition, uridine is a complement of adenine.

A 3'-O-blocked deoxynucleotide is a deoxynucleotide having attached to the 3' oxygen of its sugar component a chemical group, for example an allyl group, that precludes further polymerization from the 3' oxygen until that blocking group is removed.

This invention further provides the instant method, wherein determining whether pyrophosphate generated in step (b) (i) is performed by detecting light generated by a luciferase-based reaction. In one embodiment, the luciferase is firefly luciferase. In another embodiment, the luciferase-based reaction comprises contacting the pyrophosphate with a sulfurylase under conditions permitting the generation of ATP from the pyrophosphate, and contacting the ATP so generated with a luciferase under conditions permitting the generation of light by the luciferase in the presence of ATP. A luciferase-based reaction includes, for example, the reaction of luciferin and ATP in the presence of luciferase and $O_2$, whereby oxyluciferin, AMP, PPi, $CO_2$, and light are produced. The light produced can be measured by any standard photometry technique including, but not limited to, photomultiplier, video, CCD, CCCD, and the naked eye.

In a preferred embodiment, the moiety blocking the 3'-O atom of the dNTP is an allyl moiety and the single-stranded DNA is immobilized to a solid substrate.

In another embodiment, determining whether pyrophosphate is generated in step (b) (i) is performed by detecting dissociation of a coumarin-derived indicator from a complex between the indicator and a bis-$Zn^{2+}$-dipicolylamine coordination compound, wherein the coumarin-derived indicator has the following structure:

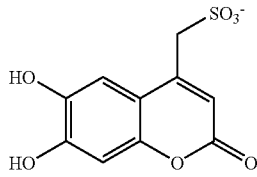

and the bis-$Zn^{2+}$-dipicolylamine coordination compound, when in association with the coumarin-derived indicator, has the following structure:

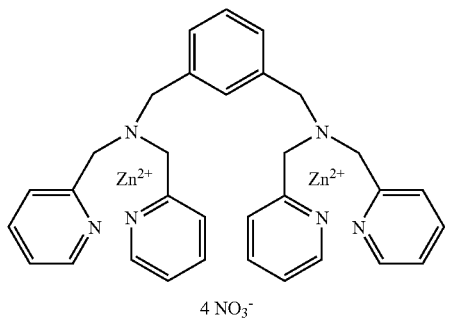 [SMILES: c1ccc(CN(Cc2cccc(CN(Cc3ccccn3)Cc3ccccn3)c2)Cc2ccccn2)nc1 ; [Zn+2] ; [Zn+2]]

In the preferred embodiment, the moiety blocking the 3'-O atom of the dNTP is an allyl moiety and the single-stranded DNA is immobilized to a solid substrate. In another embodiment the moiety blocking the 3'-O atom of the dNTP is an allyl moiety or a methoxymethyl moiety. Preferably, the moiety is an allyl moiety.

In the preferred embodiment of the instant method, the DNA is immobilized on a solid substrate. In different embodiments, the DNA is bound to the solid substrate via an azido linkage, an alkynyl linkage, a 1,3-dipolar cycloaddition linkage, or biotin-streptavidin interaction. The solid substrate can be, for example, in the form of a chip, a bead, a well, a capillary tube, or a slide. Also, for example, the solid substrate can be gold, quartz, silica, or plastic. In one embodiment of this invention, the solid substrate is porous.

Single-stranded DNA can be immobilized on a solid surface, for example a glass surface, by a 1,3-dipolar cycloaddition reaction in the presence of a Cu(I) catalyst. The DNA is labeled with an azido group at the 5' end, while the glass surface is modified by an alkynyl group. After the 1,3-dipolar cycloaddition between the azido and the alkynyl group in the presence of a Cu(I) catalyst at room temperature, the DNA is covalently attached to the surface via a stable 1,2,3-triazole linkage. The positions of the azido and the alkynyl functional groups are interchangeable. The resulting 1,2,3-triazoles are stable at aqueous conditions and high temperature.

In the preferred embodiment of the instant methods, the moiety blocking the 3'-O atom of the dNTP is an allyl moiety and removing it is performed using $Na_2PdCl_4$ and TPPTS.

This invention also provides a compound comprising a dNTP having bound to its 3' oxygen an allyl or methoxymethyl moiety. In the preferred embodiment, the moiety is an allyl moiety. In another embodiment, the moiety is a methoxymethyl moiety. In specific embodiments the dNTP is dATP, dCTP, dGTP, or dTTP. In a further embodiment, the instant compound is a 3'-O-allyl dNTP, and specifically 3'-O-allyl dATP, 3'-O-allyl dCTP, 3'-O-allyl dGTP, 3'-O-allyl dUTP or 3'-O-allyl dTTP.

Examples of allyl derivatives include, without limitation, analogs or homologs thereof, or haloallyls such as iodoallyl, chloroallyl and fluoroallyl which perform as blocking moieties. Examples of methoxymethyl derivatives include, without limitation, analogs or homologs thereof which perform as blocking moieties.

This invention also provides a process for producing a 3'-O-allyl dNTP comprising:

(a) sequentially contacting a dimethoxytrityl (DMTr) 3' protected nucleoside triphosphate with (i) 3-bromo propene, NaOH and benzene, and (ii) a suitable solvent; and (b) sequentially contacting the product of step (a) with (i) $POCl_3/(MeO)_3P(O)$, (ii) tributylammonium pyrophosphate, and (iii) $TEAB/NH_4OH$, so as to produce the 3'-O-allyl dNTP.

In one embodiment of the instant method, the suitable solvent of step (a)(ii) is 3% $THF/CHCl_3$. In another embodiment, the concentration of TEAB in step (b) (iii) is about 0.1M.

Finally, this invention provides a kit for use in sequencing a single-stranded DNA comprising:

(a) 3'-O-allyl dATP, 3'-O-allyl dCTP, 3'-O-allyl dTTP, and 3'-O-allyl dGTP, each in a separate compartment; and (b) instructions for use.

In various embodiments, the instant kit further comprises (i) a 9°N DNA polymerase (exo−) A485I/Y409V, (ii) reagents permitting DNA polymerization, (iii) reagents permitting pyrophosphate detection using a luciferase-based reaction, (iv) reagents permitting pyrophosphate detection using a coumarin-derived indicator, and/or (v) reagents permitting removal of an allyl group from a 3'-O-allyl dNTP.

In differing embodiments, the 3'-O-allyl-modified dNTP has one of the following structures:

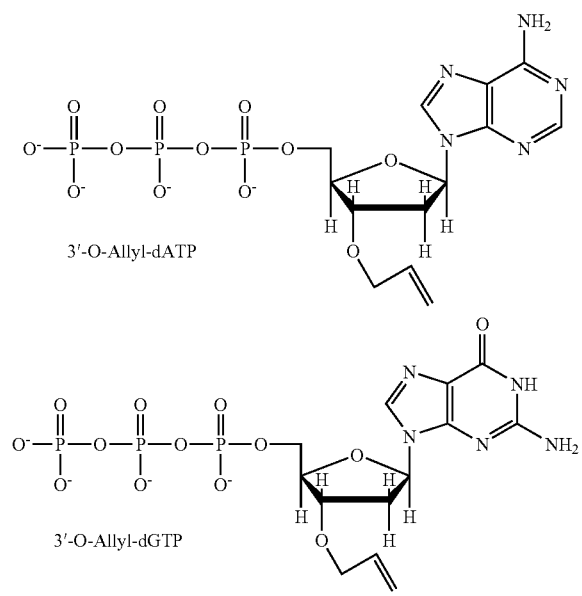

-continued

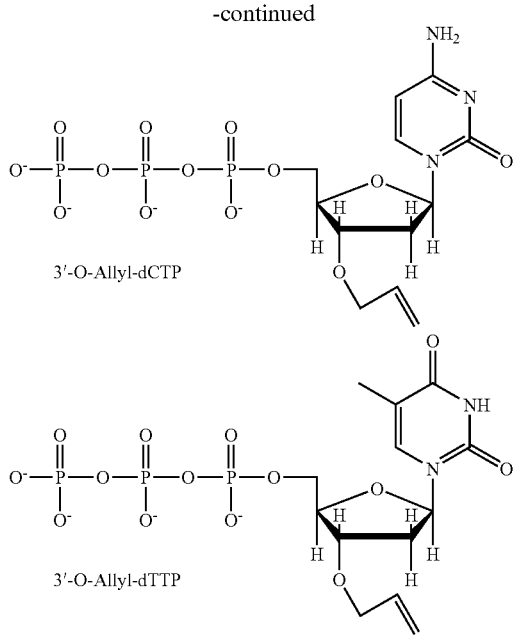

3'-O-Allyl-dCTP

3'-O-Allyl-dTTP

This invention will be better understood by reference to the Experimental Details which follow, but those skilled in the art will readily appreciate that the specific experiments detailed are only illustrative of the invention as described more fully in the claims which follow thereafter.

Experimental Details

Figure 2:
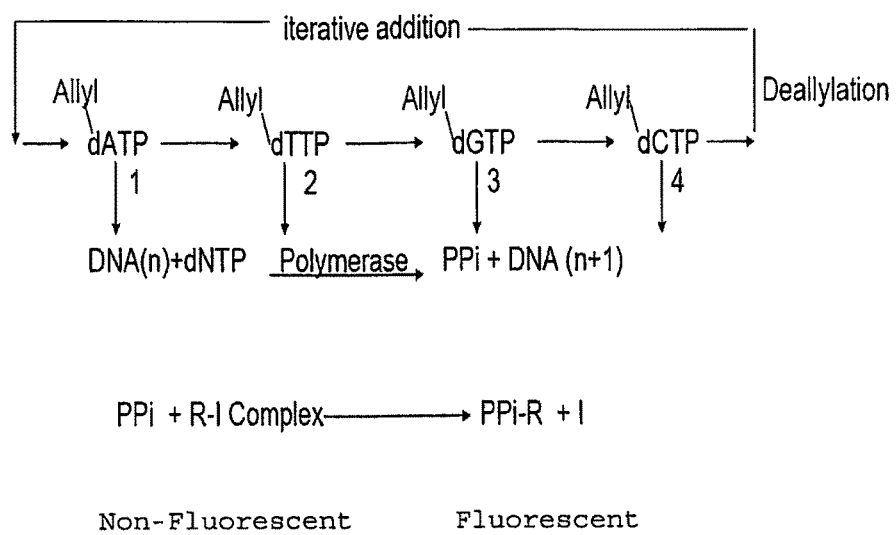
FIG. 2: 3'-O-Allyl-dNTP (A, C, G, T), instead of dNTP, is used in the single base extension on a solid surface. Four Allyl-dNTPs are added iteratively. Once the complementary base is incorporated, the pyrophosphate that is produced from the reaction can be detected by its reaction with the light-generating luciferase system or a receptor-indicator (R-I) coordination compound via the release of the fluorescent indicator molecule. Then the extended primers can be deallylated, washed and reused in the next round. The use of an allyl-group solves inherent problems of traditional pyrosequencing.

The general scheme of the improved pyrosequencing method is shown in FIG. 2. 3'-O-allyl-dNTPs (A, C, G, T), instead of dNTPs, are used in the single base extension on a solid surface. Four allyl-dNTPs are added iteratively. Once the complementary base is incorporated, the pyrophosphate that is produced from the reaction can be detected by its reaction with the light-generating luciferase system or a receptor-indicator (R-I) coordination compound via the release of the fluorescent indicator molecule. In one case the R-I compound has negligible or no fluorescence, and the released/displaced indicator is detectably fluorescent. Then the extended primers can be deallylated, washed and reused in the next round. The use of an allyl group solves inherent problems of traditional pyrosequencing.

Figure 3:
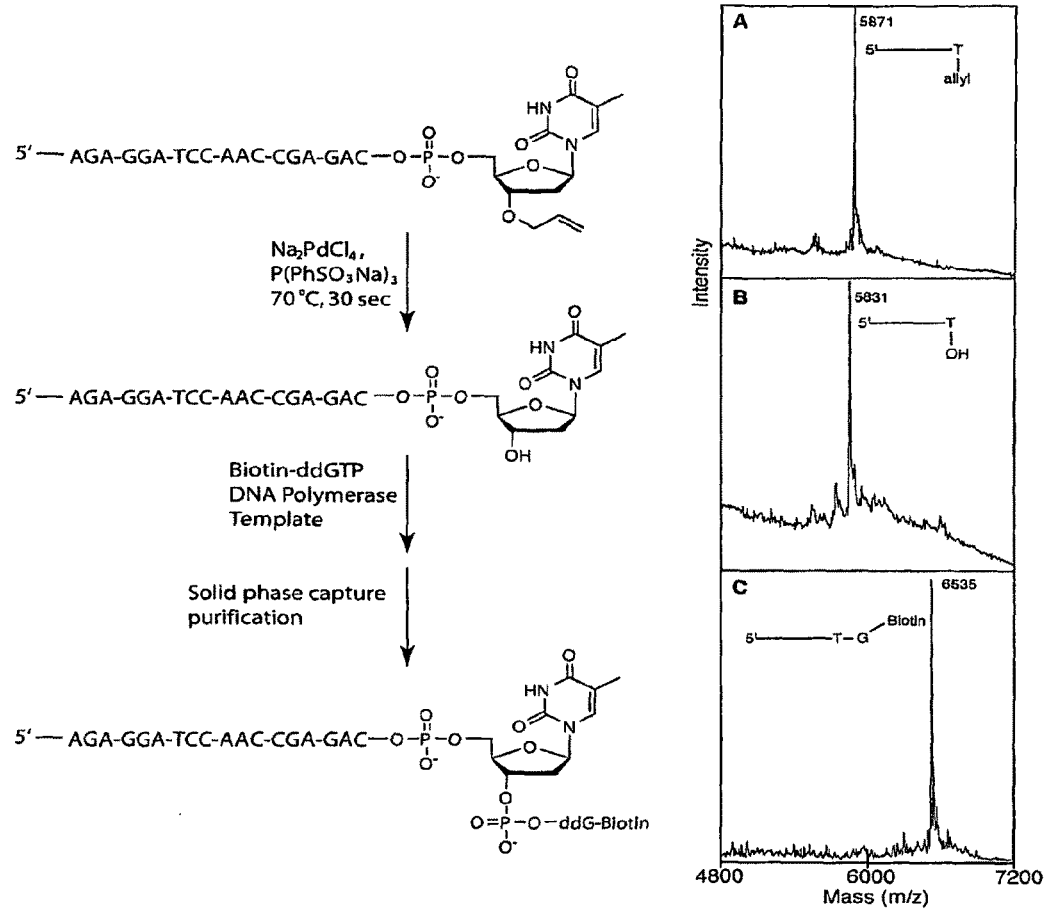
FIGS. 3A-3C: Schematic representation and step-by-step MALDI-TOF MS results for the deallylation of an allyl-modified oligonucleotide (SEQ ID NO:1) and the use of the deallylated DNA product as a primer in a polymerase extension reaction. (A) Peak at m/z 5871 corresponding to the HPLC-purified 3'-allyloxy 19-mer oligonucleotide. (B) Peak at m/z 5831 corresponding to the above DNA product without the allyl group, obtained after 30 secs of incubation with the $Na_2PdCl_4$ catalyst and the TPPTS ($P(PhSO_3Na)_3$) ligand at 70° C. (C) Peak at m/z 6535 corresponding to the extension of the deallylated DNA product by Biotin-ddGTP using Thermo Sequenase DNA Polymerase.

Synthesis and Deallylation of 3'-O-Allyl-dNTP and its Performance in Single Base Extension A mild condition to remove a 3'-O-allyl group from DNA in aqueous solution using a catalyst system formed by $Na_2PdCl_4$ and a water-soluble ligand 3,3',3''-phosphinidynetris(benzenesuifonic acid), trisodium salt (TPPTS) [3] has been identified. Using this condition, the deallylation of the purified 19-mer oligonucleotide (5'-AGAGGATCCAAC-CGAGAC-T(allyl)-3') (SEQ ID NO:8) was established using MALDI-TOF mass spectrometry. In FIG. 3A, the mass peak at m/z 5871 corresponds to the mass of the purified oligonucleotide bearing the allyl group. The deallylation reaction on this oligonucleotide was carried out using the $Na_2PdCl_4$/TPPTS system. FIG. 3B shows near complete deallylation with a DNA/catalyst/ligand ratio of 1/50/400 in a reaction time of 30 secs, as shown by the mass peak at m/z 5831.

The next step was to prove that the deallylated product could be used in a primer extension reaction and that deallylation did not hinder the continuation of the polymerase reaction. A single base extension reaction using the deallylated product as a primer was performed with a synthetic template and a Biotin-ddGTP nucleotide terminator complementary to the base immediately adjacent to the priming site on the template. The extension product was isolated using solid phase capture purification and analyzed using MALDI-TOF MS [4]. The mass spectrum in FIG. 3C shows a clear peak at m/z 6535 corresponding to the extension product proving that the deallylated product can be successfully used as a primer in a polymerase reaction.

Figure 4:
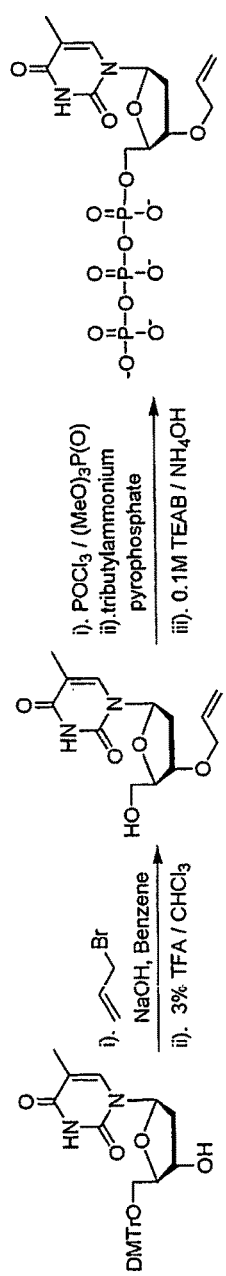
FIG. 4: Synthesis of a 3'-O-allyl-modified oligonucleotide.

These experiments established that $Na_2PdCl_4$ and TPPTS could be used to efficiently carry out deallylation on DNA in an aqueous environment without the need for an allyl scavenger or harsh conditions. A next step was to ensure that an allyl-modified nucleotide could be incorporated in a DNA Polymerase reaction. For this purpose, a nucleotide analogue 3'-allyloxythymidine triphosphate (3'-O-allyl-dTTP) was synthesized (FIG. 4) and its incorporation ability was tested using a mutant form of 9°N DNA Polymerase (exo−) bearing the mutations A485L and Y409V. Results showed that this enzyme could incorporate 3'-O-allyl-dTTP in a polymerase reaction. 3'-O-allyl-dGTP, 3'-O-allyl-dATP and 3'-O-allyl-dCTP can be similarly prepared according to the scheme set forth in FIG. 4.

Figure 5:
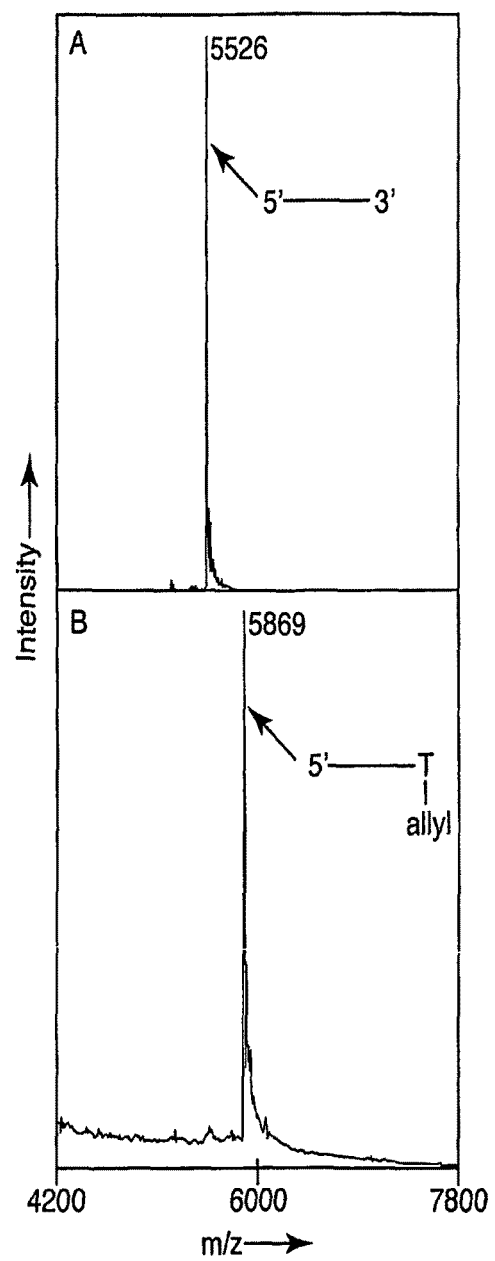
FIGS. 5A & 5B: MALDI-TOF MS spectra showing the incorporation of 3'-O-allyl-modified dTTP into a growing DNA strand by 9°N Polymerase (exo−) A485L/Y409V; (A) unextended primer at m/z 5526; (B) primer extended with 3'-O-allyl-dTTP at m/z 5869.

The 3'-O-allyl-thymidine triphosphate was used in a primer extension reaction to demonstrate its ability to be incorporated into a growing DNA strand by DNA Polymerase. The extension was performed using a 15-μl reaction mixture consisting of 50 pmol of an 18-mer primer (5'-AGA-GGA-TCC-AAC-CGA-GAC-3') (SEQ ID NO:9), 100 pmol of single-stranded 60-mer DNA template (5'-GTG-TAC-ATC-AAC-ATC-ACC-TAC-CAC-CAT-GTC-AGT-CTC-GGT-TGG-ATC-CTC-TAT-TGT-GTC-CGG-3') (SEQ ID NO:10) corresponding to a portion of exon 7 of the p53 gene (200 pmol of 3'-O-allyl-thymidine triphosphate), 1× Thermopol reaction buffer (New England Biolabs) and 15 U of 9°N DNA polymerase (exo−) A485L/Y409V. The extension reaction consisted of 15 cycles at 94° C. for 20 sec, 48° C. for 30 sec and 60° C. for 60 sec. The product was desalted using Zip Tip and analyzed using MALDI-TOF MS. The mass spectral data are shown in FIG. 5. FIG. 5(A) shows a single mass peak at m/z 5526 corresponding to the unextended primer. FIG. 5(B) shows a single peak at m/z 5869 corresponding to the primer extended by a single base 3'-O-allyl-thymidine triphosphate. These data confirm that the above 3'-allyl-modified nucleotide analogue can be efficiently incorporated by 9°N DNA polymerase (exo−) A485L/Y409V.

Single Base Extension on Solid Surface with 3'-Allyl-dNTP (Click Chemistry)

In order to separate primers from the mixture after SBE and deallylation, the primers can be immobilized on a solid surface. One common method is to use paramagnetic beads which are coated with streptavidin. Primers which are labeled with biotin can be attached to the beads because of the biotin-streptavidin attraction. A recently developed DNA immobilization method using click chemistry, [6] hereby incorporated by reference, can be used in the pyrosequencing method disclosed here. With the addition of template, ally-dNTP and polymerase, the extension can take place on the beads.

A New PPi Detection System for use in Pyrosequencing (Chemosensing Ensemble)

Figure 6:
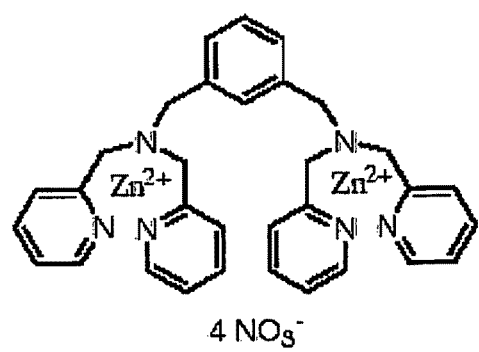
FIGS. 6A & 6B: (A) Receptor (R): $Zn^{2+}$-dipicolylamine (Zn2+DPA); (B) Indicator (I): fluorescent molecule (coumarin-derived indicator). See [5].
Figure 6:
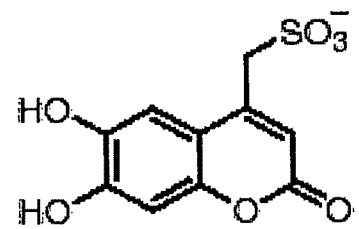
Figure 7:
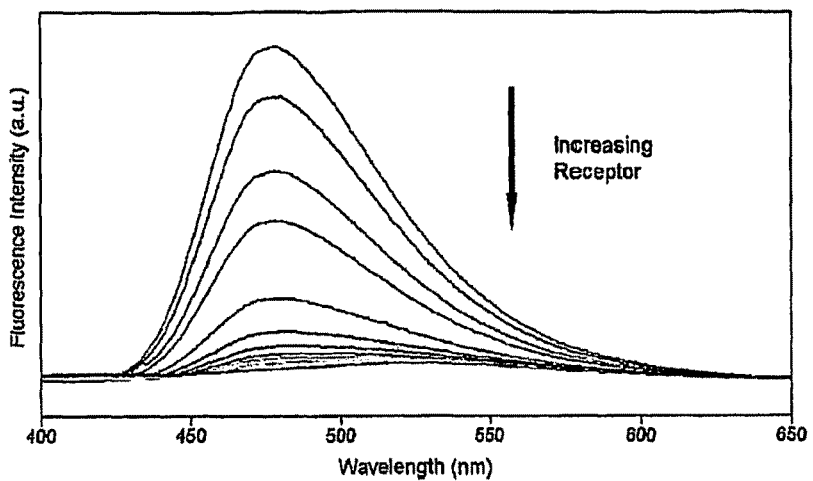
FIGS. 7A & 7B: When R is titrated into I, the fluorescence intensity of I will decrease: (A) $Zn^{2+}$DPA is titrated into (10 µM) I; (B) PPi is added to R-I coordination compound.
Figure 7:
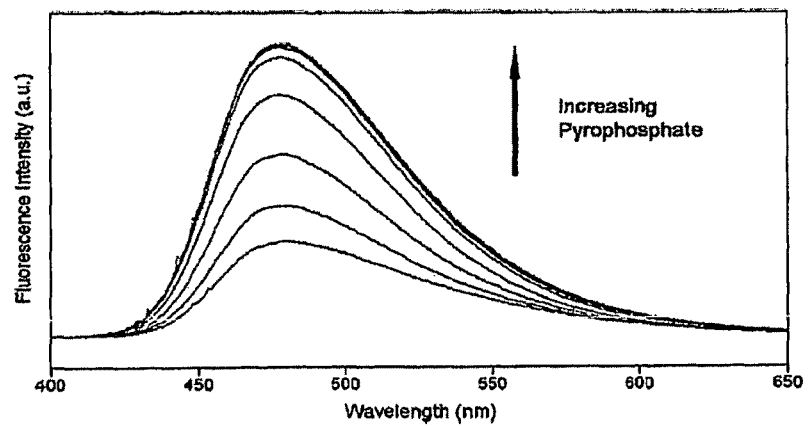

Roger reported a fluorescence chemosensing system (Chemosensing Ensemble) which is described and shown to selectively detect pyrophosphate under physiological conditions [5]. Here, pyrophosphate is capable of displacing a fluorescent coumarin-derived indicator (I) from a bis-$Zn^{2+}$-dipicolylamine ($Zn^{2+}$DPA) coordination compound (R). See FIG. 6. With an increase of the Receptor (R) amount, the non-fluorescent R-I coordination compound is formed. When the proportion of R is 50%, the fluorescence reaches its lowest, indicating a 1:1 stoichiometry. Once pyrophosphate is added to the solution, it can replace the Indicator (fluorescence molecule) from the R-I coordination compound. Therefore, the fluorescence molecule is released/displaced, and the fluorescence intensity of the solution will increase (FIGS. 7A and B).

Schematically:

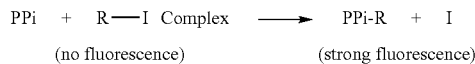

PPi + R—I Complex ⟶ PPi-R + I
(no fluorescence)                (strong fluorescence)

Using 3'-allyl-dNTPs as reversible terminators overcomes the inherent problem that the pyrosequencing method otherwise has in accurately detecting the bases in homopolymeric regions, because each base via this invention is extended one by one with high fidelity. Meanwhile, the newly designed PPi detection system is simple to use and is not affected by dATP. The paradigm of pyrosequencing can be useful in the presence of automatic sequencing machines where each step is repeated in cycles.

Improvement upon the Ronaghi Method

Ronaghi proposed a real time pyrosequencing method in solution [1]. In his method, four enzymes are needed. Among them, sulfurylase is used to transfer PPi to ATP; then luciferase is used to generate light that indicates PPi has been generated. In the next step apyrase is used to degrade ATP and excess dNTP in the reaction; then the process goes to the next round. However, apyrase activity is decreased in later cycles, which is due to the accumulation of intermediate products (such as deoxynucleoside diphosphate, or dNDP) and eventually undegraded dNTP. Because of this limitation, this method can determine the sequence of only about 100 bases at most. See FIG. 8.

Figure 8:
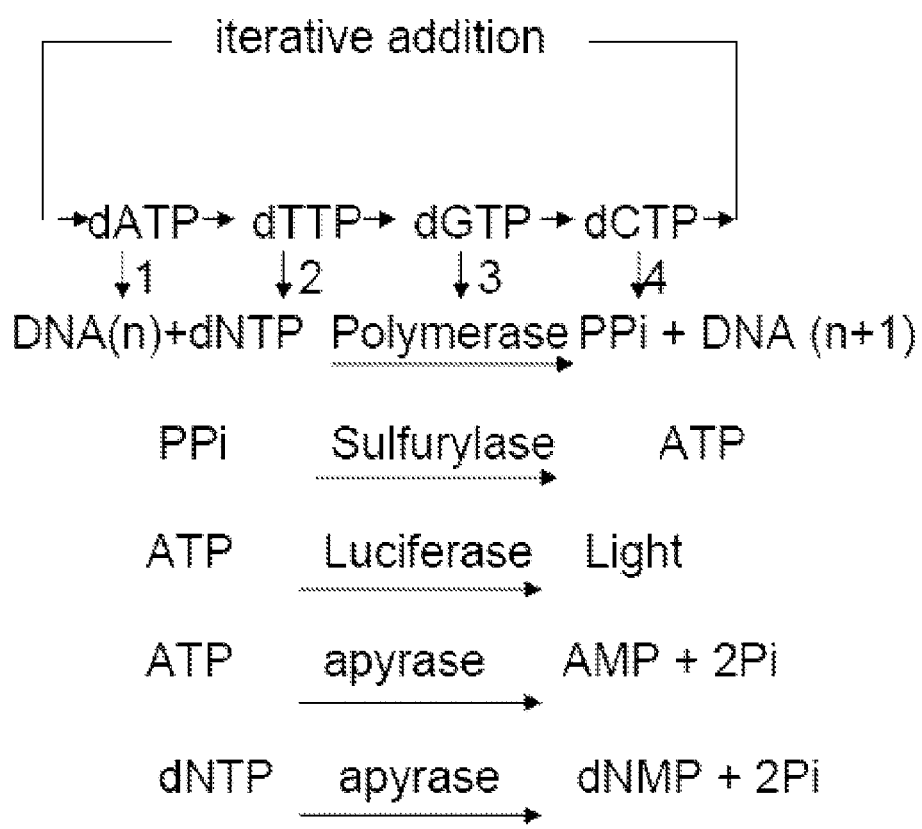
FIG. 8: Ronaghi's real-time pyrosequencing.

However, replacing dNTPs in FIG. 8 with the 3'-Allyl-dNTPs disclosed here, and then following the scheme in FIG. 8, permits one to unambiguously sequence the DNA using repeated cycles without the same degradation problems.

Figure 9:
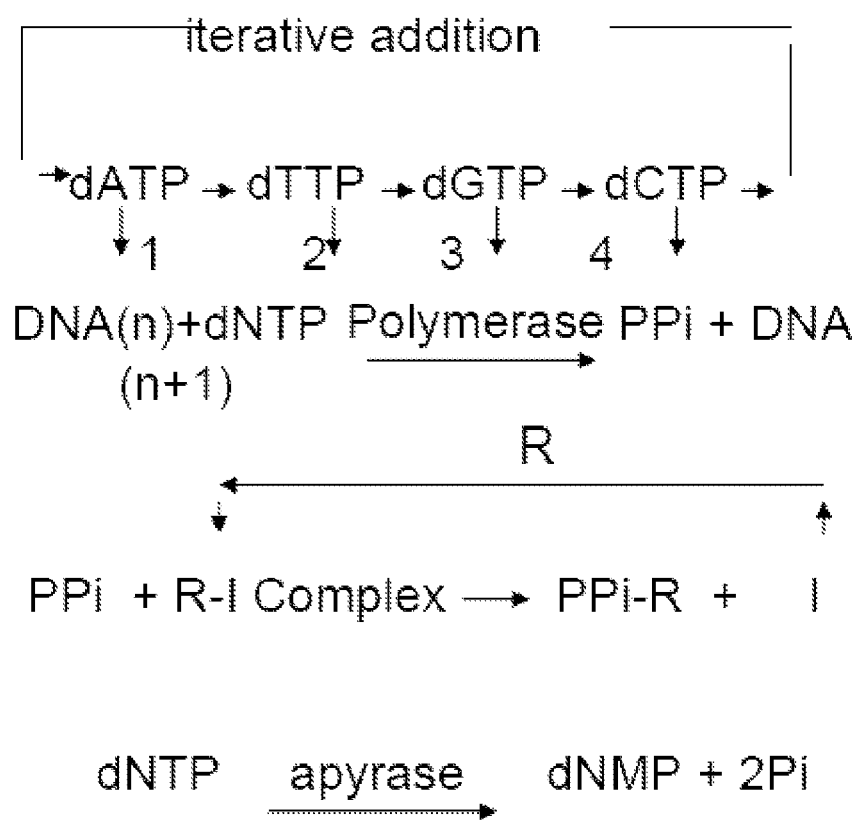
FIG. 9: Improved real-time pyrosequencing method.
Figure 10:
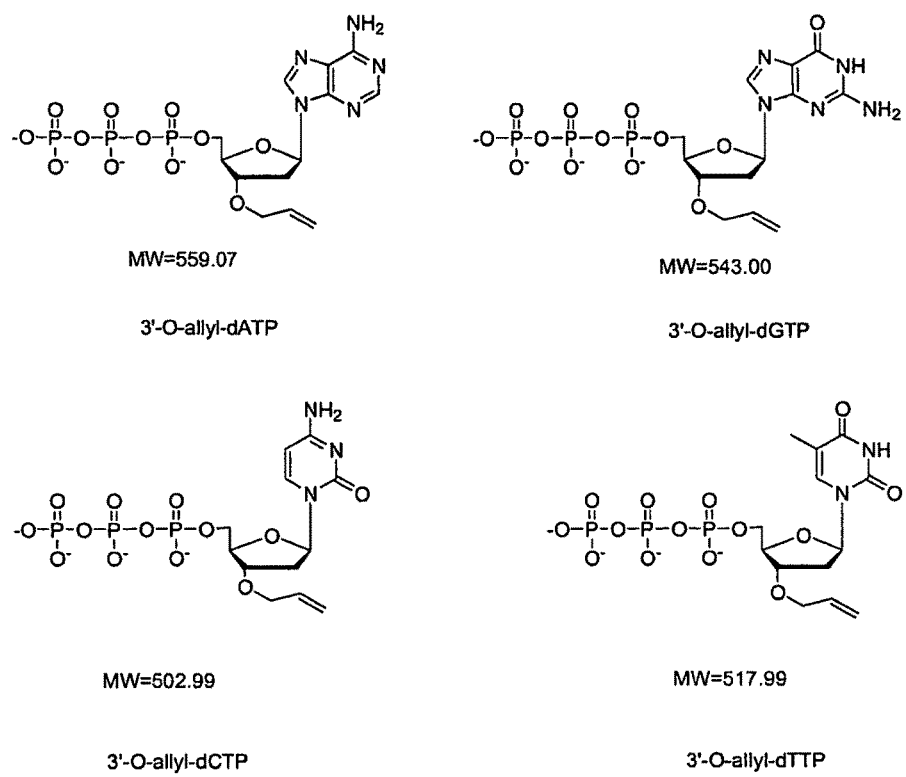
FIG. 10: Structures of four reversibly-blocked nucleotides.
Figure 11:
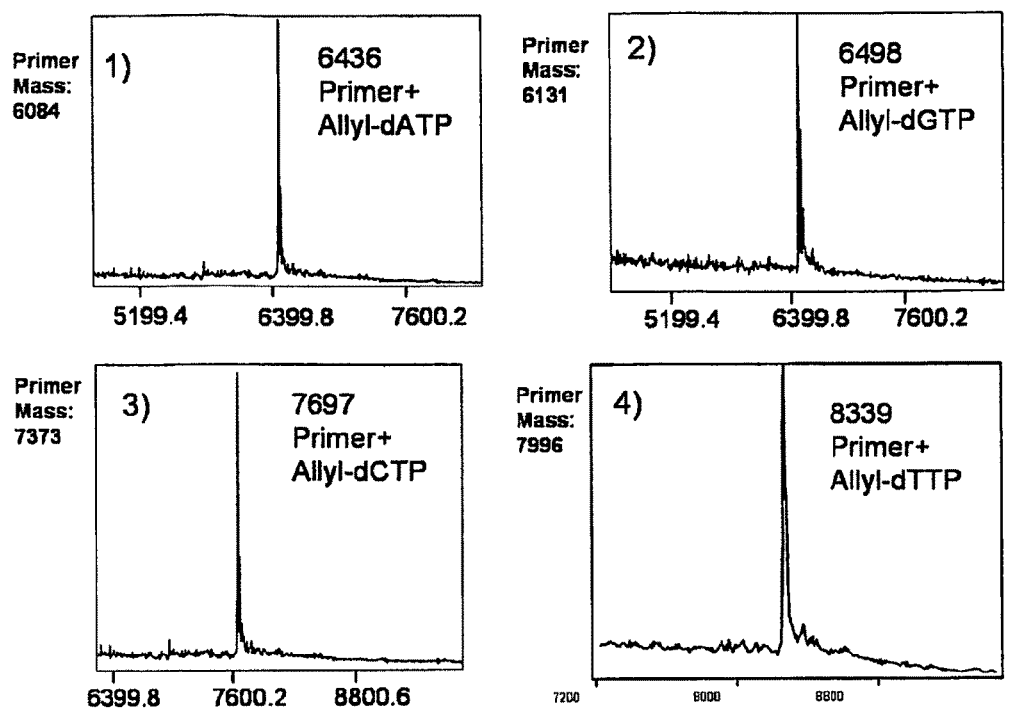
FIG. 11: Mass spectrometry traces showing incorporation of four different reversibly-blocked allyl-dNTPs into a growing DNA strand in the solution phase.
Figure 12:
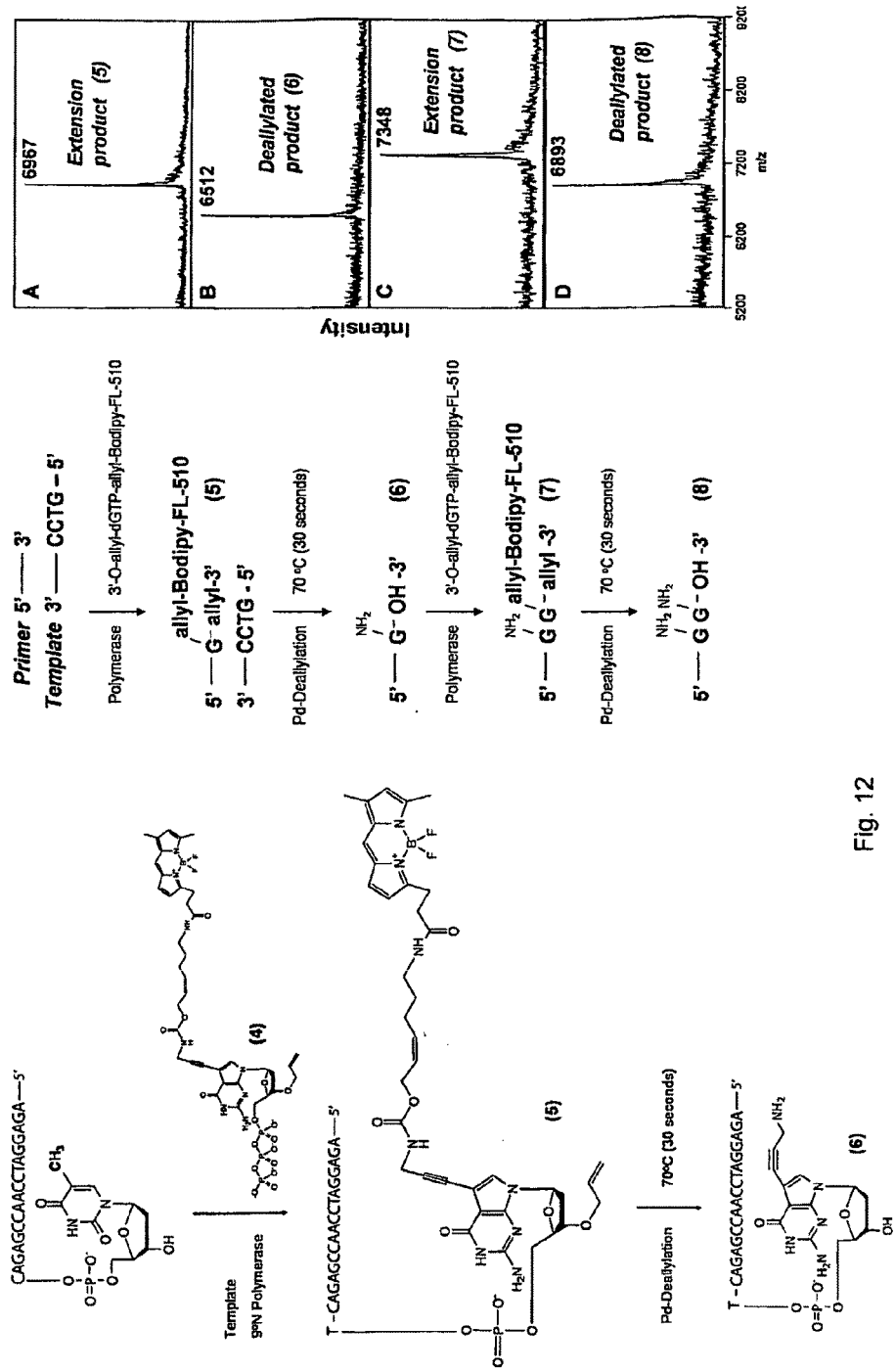
FIG. 12: Polymerase extension reaction with 3'-O-allyl-dGTP-allyl-biodipy-FL-510 as a reversible terminator of SEQ ID NO:2.
Figure 13:
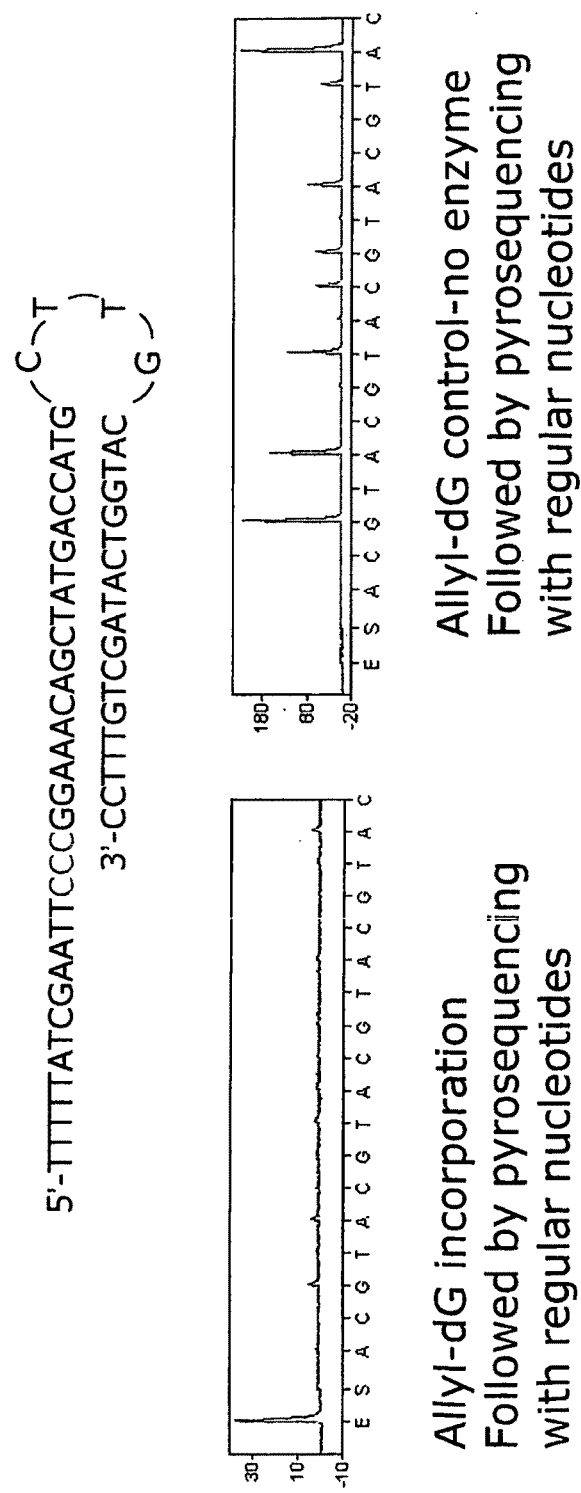
FIG. 13: Experimental results of pyrosequencing a DNA template (SEQ ID NO:3) in solution with allyl-dGTP and comparison with 'regular' unblocked nucleotides. The results indicate that allyl-dGTP is a good terminator in solution phase, and the incorporation Signal can be easily detected.
Figure 14:
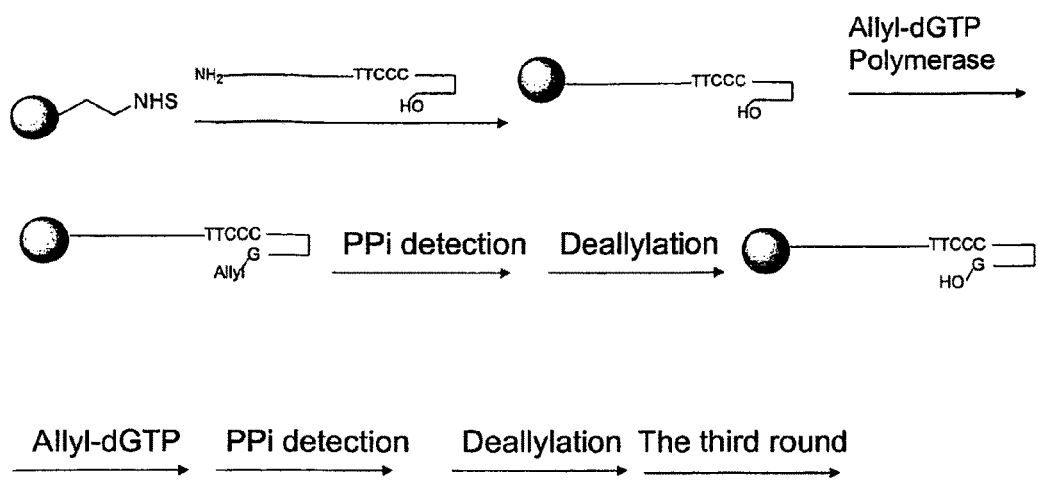
FIG. 14: An experimental scheme of a method employing allyl-dGTP for pyrosequencing with attachment of the primer (SEQ ID NO:4 and SEQ ID NO:5) to a solid surface/bead using an NHS ester.
Figure 15:
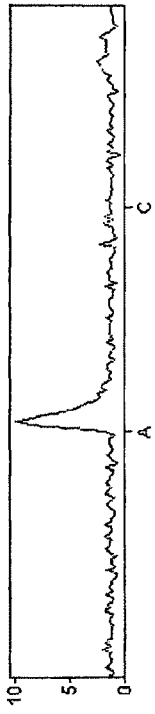
FIG. 15: Comparison of pyrosequencing using 'regular' dNTPs and pyrosequencing using reversibly-blocked dNTPS (SEQ ID NO:3).
Figure 15:
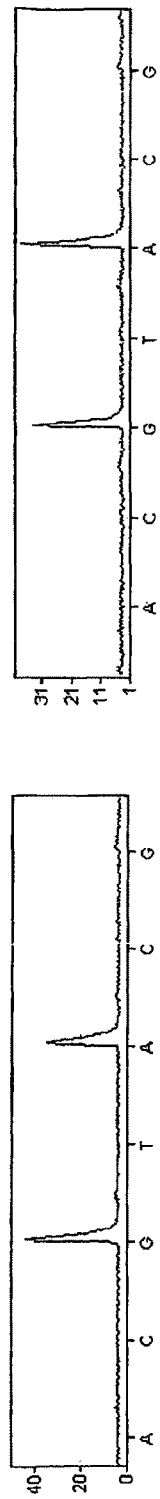
Figure 15:
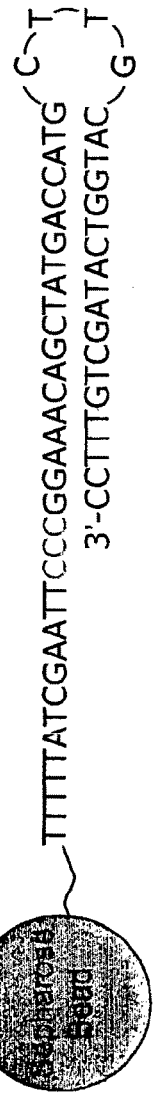
Figure 15:
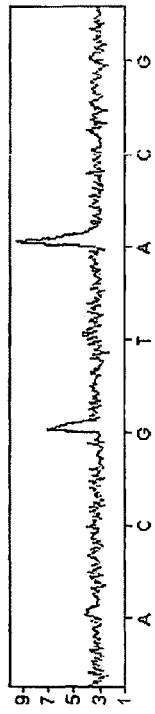
Figure 16:
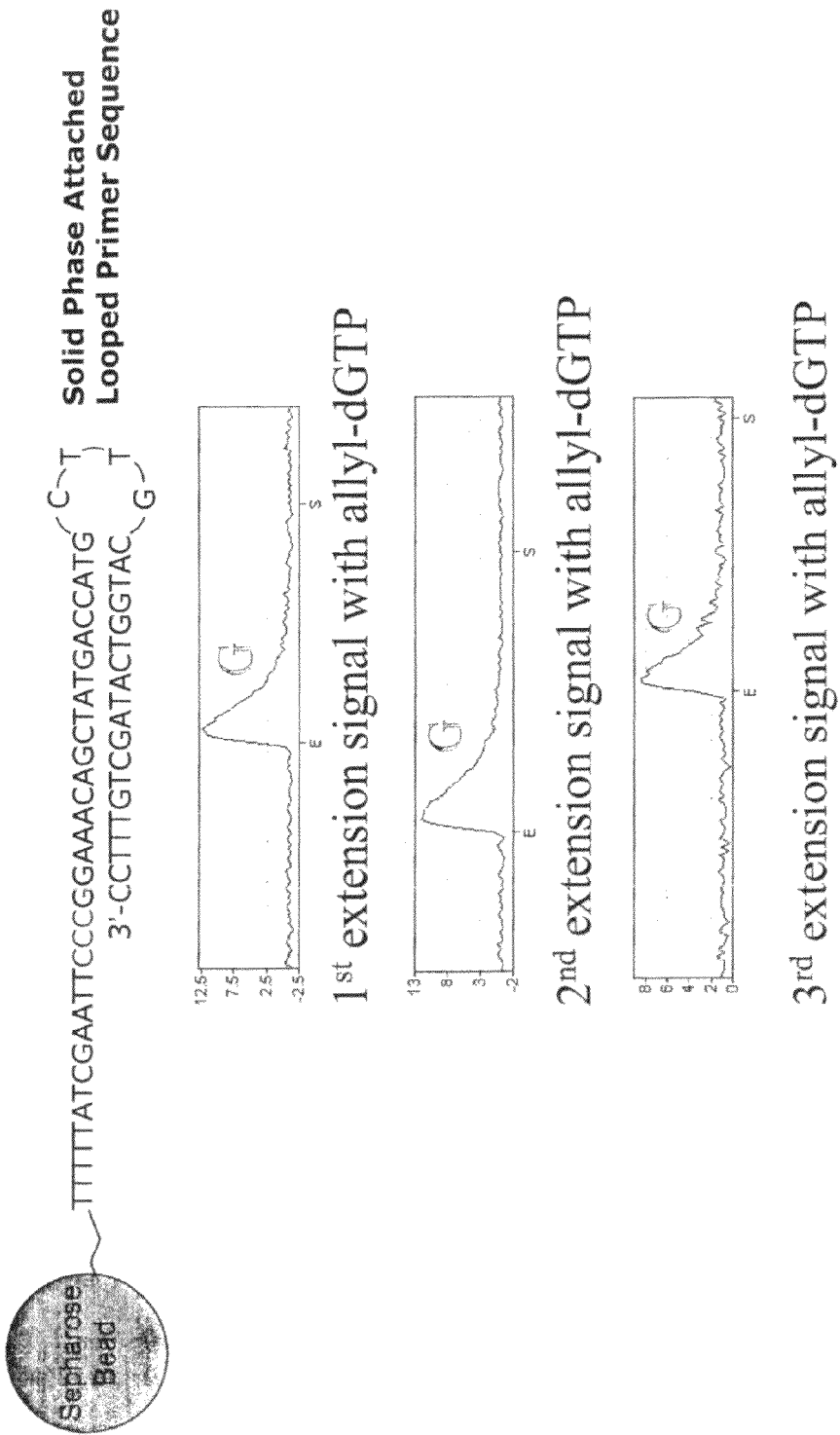
FIG. 16: Pyrosequencing data using reversible terminators on sepharose bead immobilized looped primer-DNA (SEQ ID NO:3).
Figure 17:
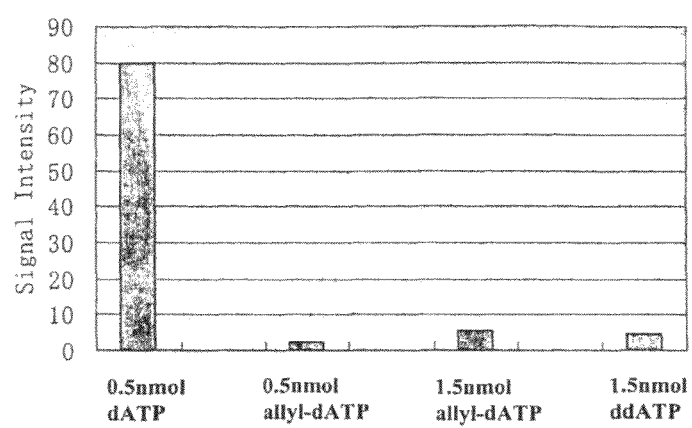
FIG. 17: Light production by luciferase in the presence of dATP and in the presence of allyl-dATP, demonstrating that allyl-dATP is not a luciferase substrate.
Figure 18:
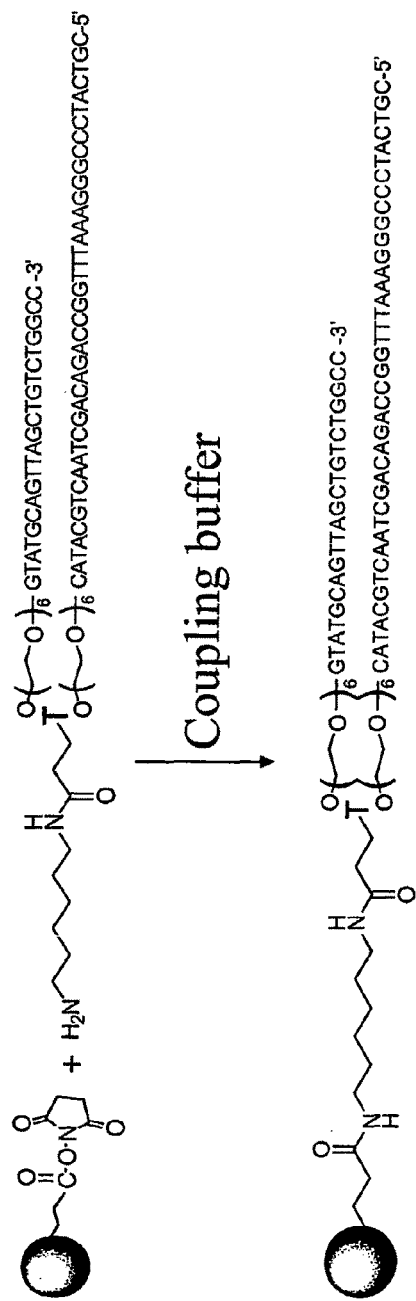
FIG. 18: Technique of immobilizing double-stranded DNA (SEQ ID NO:6 (top strand) and SEQ ID NO:7 (lower strand)) to a derivatized bead and pyrosequencing using "normal" nucleotides.
Figure 18:
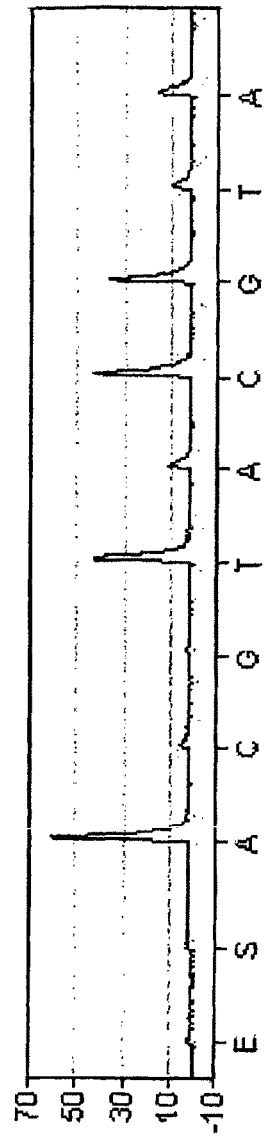
Figure 19:
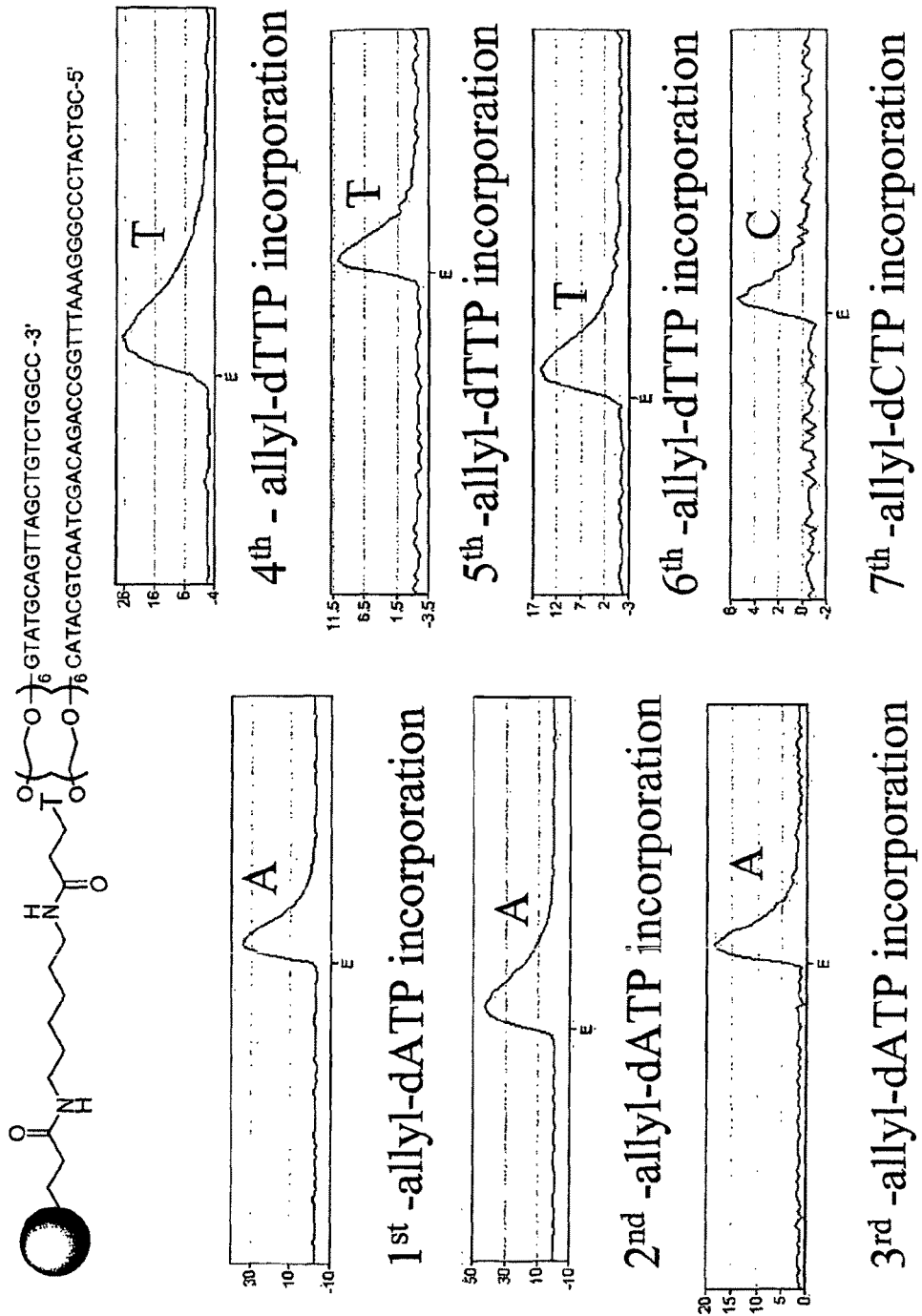
FIG. 19: Pyrosequencing on sepharose bead-immobilized DNA (SEQ ID NO:6 (top strand) and SEQ ID NO:7 (lower strand)) using Allyl-dNTPs.

The method disclosed here using the R-I complex can greatly improve the real-time pyrosequencing in the Ronaghi method. (FIG. 9). The R-I complex is used to detect PPi. PPi is converted to PPi-R, while the released indicator I can be transferred to the R-I complex by adding R without removing the components from the solution. The excess dNTP in each cycle is degraded by apyrase. Because there will be no ATP produced in the detection steps, apyrase now primarily degrades dNTP and is more efficient in its action. Accordingly, more bases can be determined.

Another advantage of this method is that only two kinds of enzymes are used here rather than four, and the detection step will not adversely affect the other steps. However, this improved method cannot detect the bases in homopolymeric regions either, and so 3'-O allyl dNTPs are employed to circumvent this problem.

REFERENCES

1. Ronaghi M., Uhlen M, Nyren P. A sequencing method based on real-time pyrophosphate. *Science* 281(5375), 363-365 (1998).
2. Ronaghi M., Karamohamed S., Pettersson B., Uhlen M., Nyren P. Real-time DNA sequencing using detection of pyrophosphate release. *Anal. Biochem.* 242(1), 84-89 (1996).
3. "Design and Synthesis of a 3'-O-Allyloxy Photocleavable Fluorescent Nucleotide as a Reversible Terminator for DNA Sequencing By Synthesis". H. Ruparel, L. Bi, Z. Li, X. Bai, D. H. Kim, N. Turro & J. Ju. *Proceedings of the National Academy of Sciences USA* 2005, 102, 5932-5937.
4. Edwards, J. R., Itagaki, Y. & Ju, J. Solid Phase Capturable Dideoxynucleotides for Multiplex Genotyping Using Mass Spectrometry (2001). *Nucleic Acids Res.* 29, e104 (p 1-6).
5. Roge G. etc. An indicator displacement system for fluorescent detection of phosphate oxyanions under physiological conditions. *Tetrahedron Letters* 45(2004) 8721-8724.
6. Ju, J. et al., U.S. Pat. No. 6,664,079.

---

What is claimed is:

1. A method for determining the nucleotide sequence of a single-stranded DNA comprising performing the following steps:

(a) immobilizing the single-stranded DNA on a solid substrate via an azido linkage, an alkynyl linkage, or a 1,2,3-triazole linkage;

(b) contacting the DNA under DNA polymerization-permitting conditions with (i) a 3'-O-blocked dNTP selected from the group consisting of 3'-O-blocked dATP, 3'-O-blocked dCTP, 3'-O-blocked dGTP, and 3'-O-blocked dTTP, wherein each 3'-O-blocked dNTP comprises an unmodified triphosphate group, and wherein each 3'-O-blocked dNTP comprises an unlabeled base, and (ii) 9° N DNA polymerase (exo-) A485I/ Y409V, wherein the moiety blocking the 3'-O atom of the dNTP is an allyl moiety or a methoxymethyl moiety;

(c) (i) determining whether pyrophosphate is generated as a result of step (b), whereby (1) pyrophosphate generation indicates that polymerization has occurred and the identity of the nucleic acid residue in the DNA is that which is complementary to the 3'-O-blocked dNTP used in part (i) of step (b), and (2) the absence of pyrophosphate generation indicates that the identity of such nucleic acid residue is not that which is complementary to such 3'-O-blocked dNTP; wherein determining whether pyrophosphate is generated is performed by detecting dissociation of a coumarin-derived indicator from a complex between the indicator and a bis-$Zn^{2+}$-dipicolylamine coordination compound, wherein the coumarin-derived indicator has the following structure:

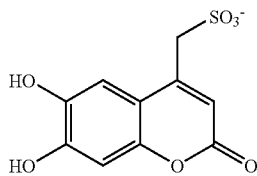

and the bis-$Zn^{2+}$-dipicolylamine coordination compound, when in association with the coumarin-derived indicator, has the following structure:

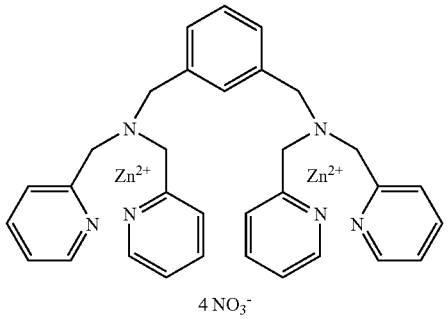 [SMILES: c1ccc(CN(Cc2cccc(CN(Cc3ccccn3)Cc3ccccn3)c2)Cc2ccccn2)nc1 ; [Zn+2] ; [Zn+2]]

and (ii) if pyrophosphate is not generated, repeating step (b) once, twice or three times as necessary, wherein in each repetition a 3'-O-blocked dNTP is used which is different from any 3'-O-blocked dNTP already used, and determining, after each repetition of step (b), whether pyrophosphate is generated, such generation indicating that polymerization has occurred and the identity of the nucleic acid residue in the DNA is that which is complementary to the 3'-O-blocked dNTP used in part (i) of the repeated step (b); and
wherein excess dNTPs are degraded by apyrase;

(d) removing from the 3'-O-blocked dNTP polymerized in step (b) or (c), whichever is applicable, the moiety blocking the 3'-O atom of the dNTP, with the proviso that such removing step is optional in the event that there remains no further nucleic acid residue of the DNA whose identity is to be determined; and (e) iteratively repeating each of steps (b) to (d) for each nucleic acid residue of the single-stranded DNA whose identity is to be determined, thereby determining the sequence of the single-stranded DNA.

2. The method of claim 1, wherein the moiety is an allyl moiety.

3. The method of claim 1, wherein the moiety blocking the 3'-O atom of the dNTP is an allyl moiety and removing it is performed using $Na_2PdCl_4$ and 3,3',3''-phosphinidynetris (benzenesulfonic acid), trisodium salt (TPPTS).

4. The method of claim 1, wherein the solid substrate is in the form of a chip, a bead, a well, a capillary tube, or a slide.

5. The method of claim 1, wherein the solid substrate is gold, quartz, silica, or plastic.

6. The method of claim 1, wherein the solid substrate is porous.

* * * * *